(12) United States Patent
Dacquay et al.

(10) Patent No.: US 8,118,790 B2
(45) Date of Patent: Feb. 21, 2012

(54) BATTERY OPERATED SURGICAL HAND PIECE WITH DISPOSABLE END

(75) Inventors: Bruno Dacquay, Irvine, CA (US); Casey Lind, Irvine, CA (US); Cesario Dos Santos, Aliso Viejo, CA (US); Paul R. Hallen, Colleyville, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 188 days.

(21) Appl. No.: 12/443,898

(22) PCT Filed: Oct. 9, 2007

(86) PCT No.: PCT/US2007/080751
§ 371 (c)(1),
(2), (4) Date: Apr. 1, 2009

(87) PCT Pub. No.: WO2008/105957
PCT Pub. Date: Sep. 4, 2008

(65) Prior Publication Data
US 2010/0211044 A1     Aug. 19, 2010

Related U.S. Application Data

(63) Continuation-in-part of application No. 11/435,906, filed on May 17, 2006.

(60) Provisional application No. 60/921,497, filed on Oct. 16, 2006, provisional application No. 60/921,498, filed on Oct. 16, 2006, provisional application No. 60/921,499, filed on Oct. 16, 2006.

(51) Int. Cl.
*A61M 35/00*    (2006.01)

(52) U.S. Cl. .................... 604/294; 604/113; 604/291

(58) Field of Classification Search .................. 604/114, 604/131, 67, 521
See application file for complete search history.

(56) References Cited

U.S. PATENT DOCUMENTS 1,252,614 A    1/1918   Pieper et al.
(Continued)

FOREIGN PATENT DOCUMENTS

AU    7623298    6/1998
(Continued)

OTHER PUBLICATIONS

U.S. Appl. No. 11/200,452, filed Aug. 9, 2005, Hopkins.
(Continued)

*Primary Examiner* — Jackie Ho
*Assistant Examiner* — Imani Hayman
(74) *Attorney, Agent, or Firm* — Kenneth D. Bassinger

(57) ABSTRACT

The present invention is an ophthalmic injection system with a limited reuse assembly and a tip segment. The tip segment is connectable to and removable from the limited reuse assembly. The tip segment includes a dispensing chamber, a plunger, and a housing. The dispensing chamber holds a quantity of a substance to be injected into an eye. The proximate end of the plunger has a first mechanical linkage interface. The limited reuse assembly of the ophthalmic injection system has a power source, a controller, a motor, a second mechanical linkage interface located on an end of the motor shaft; and a second housing. The first mechanical linkage interface is mateable with the second mechanical linkage interface such that when the tip segment is connected to the limited reuse assembly, the first mechanical linkage interface mates with the second mechanical linkage interface so that motion of the shaft results in motion of the plunger.

46 Claims, 15 Drawing Sheets

U.S. PATENT DOCUMENTS

| | | |
|---|---|---|
| 3,089,815 A | 5/1963 | Lieb et al. |
| 3,199,740 A | 8/1965 | Huffa et al. |
| 3,608,549 A | 9/1971 | Merrill |
| 3,858,581 A | 1/1975 | Kamen |
| 3,892,537 A | 7/1975 | Gulati et al. |
| 3,982,537 A | 9/1976 | Bucalo |
| 4,007,742 A | 2/1977 | Banko |
| 4,030,499 A | 6/1977 | Bucalo |
| 4,054,138 A | 10/1977 | Bucalo |
| 4,122,850 A | 10/1978 | Bucalo |
| 4,184,510 A | 1/1980 | Murry et al. |
| 4,246,932 A | 1/1981 | Raines |
| 4,265,618 A | 5/1981 | Herskovitz et al. |
| 4,357,136 A | 11/1982 | Herskovitz et al. |
| 4,392,827 A | 7/1983 | Martin |
| 4,474,752 A | 10/1984 | Haslam et al. |
| 4,484,915 A | 11/1984 | Tartaglia |
| 4,582,488 A | 4/1986 | Newman |
| 4,684,344 A | 8/1987 | Brockway et al. |
| 4,704,088 A | 11/1987 | Newman |
| 4,713,446 A | 12/1987 | DeVore et al. |
| 4,764,165 A | 8/1988 | Reimels et al. |
| 4,795,423 A | 1/1989 | Osterholm |
| 4,830,855 A | 5/1989 | Stewart |
| 4,911,161 A | 3/1990 | Schechter |
| 4,992,045 A | 2/1991 | Beisel |
| 5,066,276 A | 11/1991 | Wang |
| 5,120,307 A | 6/1992 | Wang |
| 5,328,481 A | 7/1994 | Wang |
| 5,336,175 A | 8/1994 | Mames |
| 5,360,413 A | 11/1994 | Leason et al. |
| 5,370,630 A | 12/1994 | Smidebush et al. |
| 5,431,630 A | 7/1995 | Leonard |
| 5,476,511 A | 12/1995 | Gwon et al. |
| 5,487,725 A | 1/1996 | Peyman |
| 5,503,144 A | 4/1996 | Bacon |
| 5,582,595 A | 12/1996 | Haber et al. |
| 5,602,188 A | 2/1997 | Nakanishi |
| 5,620,700 A | 4/1997 | Berggren et al. |
| 5,662,612 A | 9/1997 | Niehoff |
| 5,743,886 A | 4/1998 | Lynn et al. |
| 5,773,019 A | 6/1998 | Ashton et al. |
| 5,783,205 A | 7/1998 | Berggren et al. |
| 5,824,072 A | 10/1998 | Wong |
| 5,860,949 A | 1/1999 | Chen |
| 5,882,338 A * | 3/1999 | Gray ............................. 604/131 |
| 5,928,197 A * | 7/1999 | Niehoff ........................ 604/155 |
| 5,928,663 A | 7/1999 | Peyman |
| 5,984,889 A | 11/1999 | Christ et al. |
| 6,051,011 A | 4/2000 | Weidenbenner |
| 6,165,190 A | 12/2000 | Nguyen |
| 6,210,357 B1 | 4/2001 | Morris |
| 6,221,045 B1 | 4/2001 | Duchon et al. |
| 6,270,343 B1 | 8/2001 | Martin |
| 6,290,690 B1 | 9/2001 | Huculak et al. |
| 6,311,868 B1 | 11/2001 | Krietemeier et al. |
| 6,364,865 B1 | 4/2002 | Lavi et al. |
| 6,372,245 B1 | 4/2002 | Bowman et al. |
| 6,372,246 B1 | 4/2002 | Wei et al. |
| 6,413,245 B1 | 7/2002 | Yaacobi et al. |
| 6,419,656 B1 | 7/2002 | Vetter et al. |
| 6,436,143 B1 | 8/2002 | Ross et al. |
| 6,488,659 B1 | 12/2002 | Rosenman |
| 6,520,930 B2 | 2/2003 | Critchlow et al. |
| 6,585,700 B1 | 7/2003 | Trocki et al. |
| 6,595,979 B1 | 7/2003 | Epstein et al. |
| 6,620,189 B1 | 9/2003 | Machoold, et al. |
| 6,635,267 B1 | 10/2003 | Miyoshi et al. |
| 6,645,179 B1 | 11/2003 | Ishikawa et al. |
| 6,726,654 B2 | 4/2004 | Rosenman |
| 6,940,209 B2 | 9/2005 | Henderson |
| 6,991,457 B2 | 1/2006 | Kazen et al. |
| 7,176,030 B2 | 2/2007 | Faries, Jr. et al. |
| 2002/0055720 A1 | 5/2002 | Hohlfelder et al. |
| 2003/0055380 A1 | 3/2003 | Flaherty |
| 2003/0125665 A1 | 7/2003 | Rosenman |
| 2004/0039253 A1 | 2/2004 | Peyman et al. |
| 2004/0052761 A1 | 3/2004 | Vernon et al. |
| 2004/0054319 A1 | 3/2004 | Langley et al. |
| 2004/0133155 A1 | 7/2004 | Varner et al. |
| 2004/0167466 A1 | 8/2004 | Drasler et al. |
| 2004/0176720 A1 | 9/2004 | Kipfer |
| 2004/0204673 A1 | 10/2004 | Flaherty |
| 2004/0210200 A1 | 10/2004 | Gerondale et al. |
| 2004/0231667 A1 | 11/2004 | Horton et al. |
| 2005/0065477 A1 | 3/2005 | Jost |
| 2005/0177137 A1 | 8/2005 | Kipfer |
| 2006/0047250 A1 | 3/2006 | Hickingbotham |
| 2007/0016186 A1 | 1/2007 | LoRusso |
| 2007/0142769 A1 | 6/2007 | Griffiths et al. |
| 2009/0069806 A1 | 3/2009 | De La Mora Levy et al. |
| 2009/0254045 A1 | 10/2009 | Jost |

FOREIGN PATENT DOCUMENTS

| | | |
|---|---|---|
| CA | 1313802 | 2/1993 |
| DE | 3434930 A1 | 4/1986 |
| EP | 0348146 A1 | 6/1989 |
| EP | 0356372 A2 | 2/1990 |
| EP | 0398394 | 11/1990 |
| EP | 0 516 292 | 2/1992 |
| EP | 1704840 A1 | 9/2006 |
| GB | 1551767 | 5/1979 |
| JP | 2002/059055 A | 2/2002 |
| RU | 2003117780 | 12/2004 |
| SU | 285170 | 10/1970 |
| WO | WO 82/03761 | 11/1982 |
| WO | WO 87/00029 | 1/1987 |
| WO | WO 93/11818 | 6/1993 |
| WO | WO 96/03978 | 2/1996 |
| WO | WO 99/33853 | 7/1999 |
| WO | WO 99/65548 | 12/1999 |
| WO | WO 00/74752 A1 | 12/2000 |
| WO | WO 01/10482 A1 | 2/2001 |
| WO | WO 02/07658 A1 | 1/2002 |
| WO | WO 03/006098 | 1/2003 |
| WO | WO 2006/037969 | 4/2006 |
| WO | WO 2006/050008 A1 | 5/2006 |
| WO | WO 2006/067480 | 6/2006 |
| WO | WO 2006/108026 A2 | 10/2006 |

OTHER PUBLICATIONS

U.S. Appl. No. 11/435,906, filed May 17, 2005, Dacquay, et al.
U.S. Appl. No. 11/486,870, filed Jul. 14, 2006, Marsh, et al.
"Ultra (TM) 2800 positive displacement;" 2004; EFD, Inc. Brochure XP 1104 vol. 11.10; 2 pages.
"Parker: Your Resource for Motion and Fluid Control Components, Systems and Solutions—System Solutions for Life Sciences;" 2003; Aurora Instruments, LLC Brochure; 8 pages.
U.S. Appl. No. 11/200,452, filed Aug. 9, 2005, Hopkins.
U.S. Appl. No. 11/435,906, filed May 17, 2005, Dacquay, et al.
U.S. Appl. No. 11/486,870, filed Jul. 14, 2006, March, et al.

* cited by examiner ated Oct. 16, 2006 and U.S. Patent Application No. 60/921,
BATTERY OPERATED SURGICAL HAND PIECE WITH DISPOSABLE END

RELATED APPLICATIONS

This application is a continuation-in-part of U.S. patent application Ser. No. 11/435,906 filed May 17, 2006, and claims the benefit of U.S. Patent Application No. 60/921,497 filed Oct. 16, 2006, U.S. Patent Application No. 60/921,498 filed Oct. 16, 2006 and U.S. Patent Application No. 60/921,499 filed Oct. 16, 2006. This Application is also a US National Stage under 35 U.S.C. 371 of PCT/US2007/080751 filed Oct. 9, 2007.

FIELD OF THE INVENTION

The present invention relates to a device for injecting a drug into an eye and more particularly to a two-piece ophthalmic drug delivery device with a disposable tip end.

BACKGROUND OF THE INVENTION

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically manually made using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to puncture the eye tissue with the needle, hold the syringe steady, and actuate the syringe plunger (with or without the help of a nurse) to inject the fluid into the eye. The volume injected is typically not controlled in an accurate manner because the vernier on the syringe is not precise relative to the small injection volume. Fluid flow rates are uncontrolled. Reading the vernier is also subject to parallax error. Tissue damage may occur due to an "unsteady" injection. In addition, when the needle is removed from the eye, the drug may be drawn out of the wound if the plunger is retracted. Such reflux leads to imprecise dosing.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. With this type of dispenser, the volumes delivered are highly dependent on fluid viscosity, surface tension, and the specific dispensing tip. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. While precise, this dispenser is expensive and requires an electrical signal to be delivered to the dispensing mechanism.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

Despite these efforts, a need remains for a dependable, low cost system for injecting precise volumes of substances into the eye without reflux.

SUMMARY OF THE INVENTION

In one embodiment consistent with the principles of the present invention, the present invention is an ophthalmic injection system including a limited reuse assembly and a tip segment. The tip segment is connectable to and removable from the limited reuse assembly. The tip segment includes a dispensing chamber, a plunger, and a housing. The dispensing chamber has an inner surface and an outer surface. The inner surface defines a cavity for receiving a quantity of a substance. The plunger is engaged with the inner surface of the dispensing chamber. The plunger is capable of sliding in the cavity of the dispensing chamber and is fluidly sealed to the inner surface of the dispensing chamber. The plunger has a proximate end and a distal end. The proximate end has a first mechanical linkage interface. The housing at least partially encloses the dispensing chamber and the plunger.

The limited reuse assembly of the ophthalmic injection system has a power source, a controller for controlling the operation of the system, a motor with a shaft, a second mechanical linkage interface located on an end of the shaft; and a second housing at least partially enclosing the controller and the motor. The first mechanical linkage interface is mateable with the second mechanical linkage interface such that when the tip segment is connected to the limited reuse assembly, the first mechanical linkage interface mates with the second mechanical linkage interface so that motion of the shaft results in motion of the plunger.

In another embodiment consistent with the principles of the present invention, the present invention is a disposable drug delivery device including a dispensing chamber, a plunger, and a housing. The dispensing chamber has an inner surface and an outer surface. The inner surface defines a cavity for receiving a quantity of a substance. The plunger is engaged with the inner surface of the dispensing chamber, is capable of sliding in the cavity of the dispensing chamber, and is fluidly sealed to the inner surface of the dispensing chamber. The plunger has a proximate end and a distal end. The proximate end has a mechanical linkage interface. The housing at least partially encloses the dispensing chamber and the plunger. The mechanical linkage is mateable with and separable from a limited reuse assembly adapted to drive the plunger.

In another embodiment consistent with the principles of the present invention, the present invention is an ophthalmic injection system including a tip segment and a limited reuse assembly. The tip segment is connectable to and removable from the limited reuse assembly. The tip segment includes a dispensing chamber, a plunger, and a motor. The dispensing chamber has an inner surface and an outer surface. The inner surface defines a cavity for receiving a quantity of a substance. The plunger is engaged with the inner surface of the dispensing chamber, is capable of sliding in the cavity of the dispensing chamber, and is plunger fluidly sealed to the inner surface of the dispensing chamber. The motor is connected to the plunger and is configured to move the plunger in a direction toward an end of the dispensing chamber.

The limited reuse assembly of the ophthalmic injection system includes an interface for connecting the tip segment to the limited reuse assembly, a controller for controlling the operation of the system; and a power source for providing power to the motor. When the tip segment is connected to the limited reuse assembly, the controller controls the operation of the motor.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
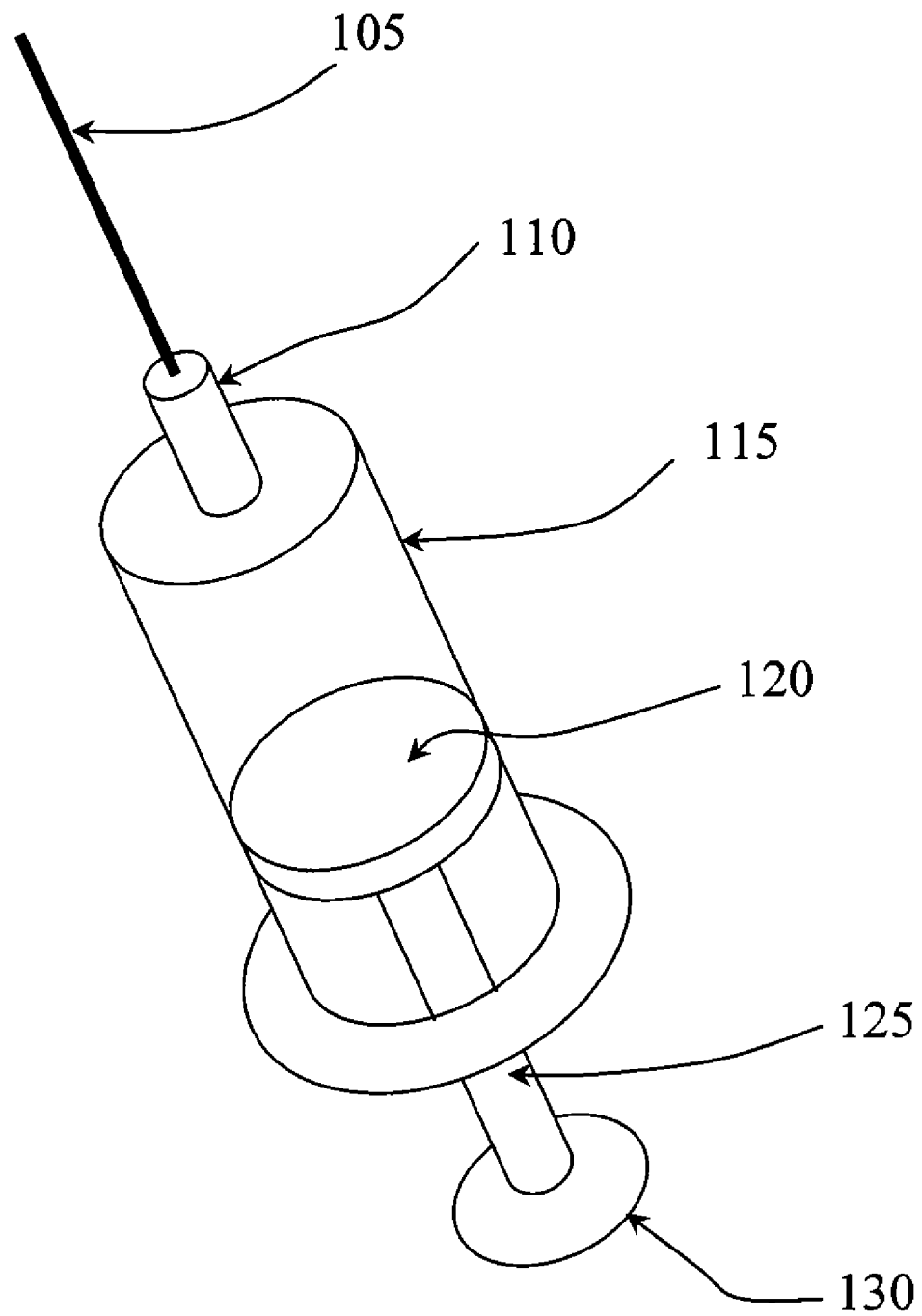
FIG. 1 is a perspective view of a prior art syringe.
Figure 2:
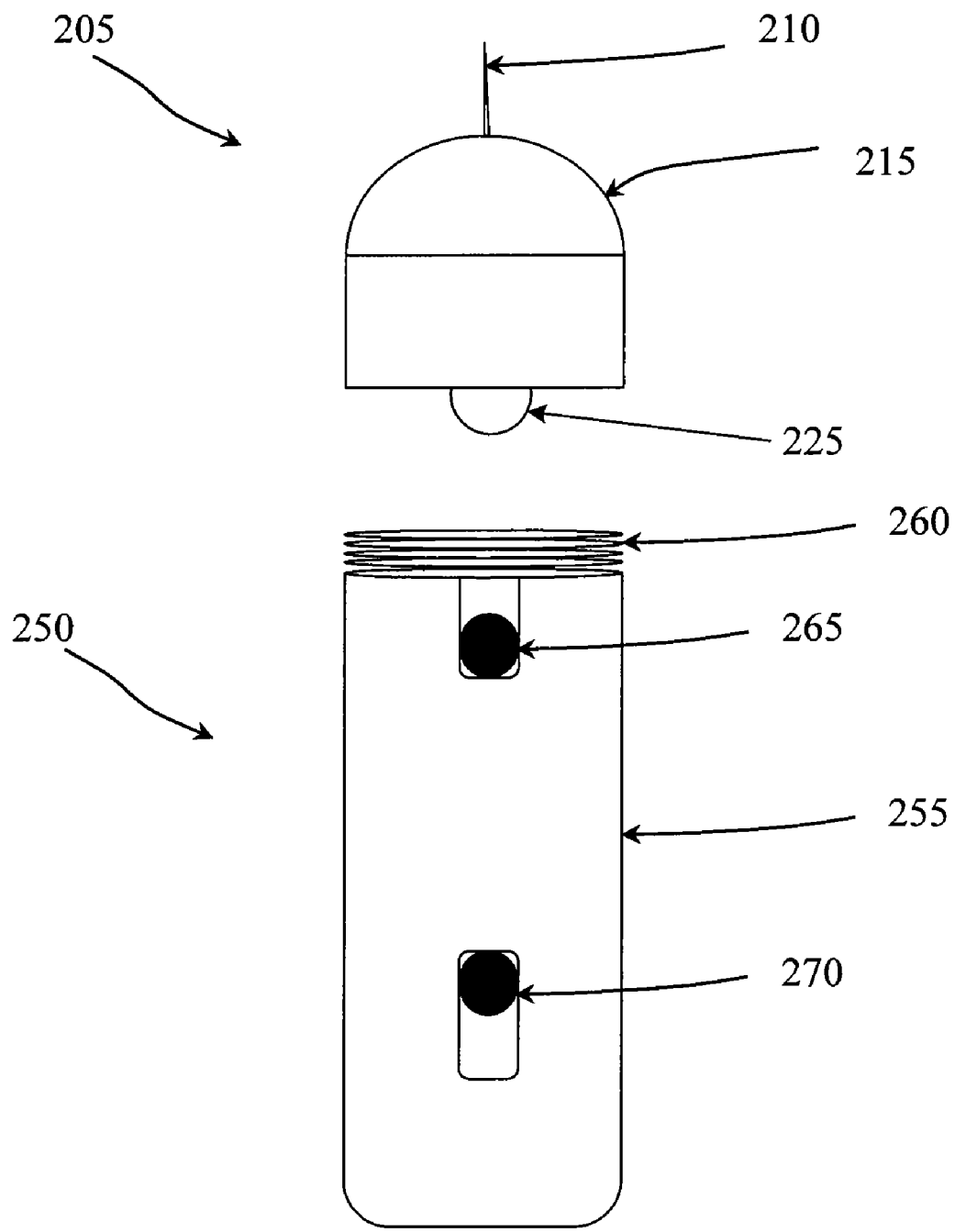
FIG. 2 is a view of an ophthalmic hand piece including a drug delivery tip segment and a limited reuse assembly according to an embodiment of the present invention.

FIG. 2 depicts one view of an ophthalmic hand piece including a drug delivery tip segment and a limited reuse assembly according to an embodiment of the present invention. In FIG. 2, the hand piece includes a tip segment 205 and a limited reuse assembly 250. The tip segment 205 includes a needle 210, a housing 215, and a plunger connection 225. The limited reuse assembly 250 includes a housing 255, a switch 270, a lock mechanism 265, and a threaded portion 260.

The tip segment 205 is capable of being connected to and removed from the limited reuse assembly 250. In this embodiment, the tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button or a sliding switch.

Needle 210 is adapted to deliver a substance, such as a drug, into an eye. Switch 270 is adapted to provide an input to the system. For example, switch 270 may be used to activate the system or to turn on a heater.

Figure 3:
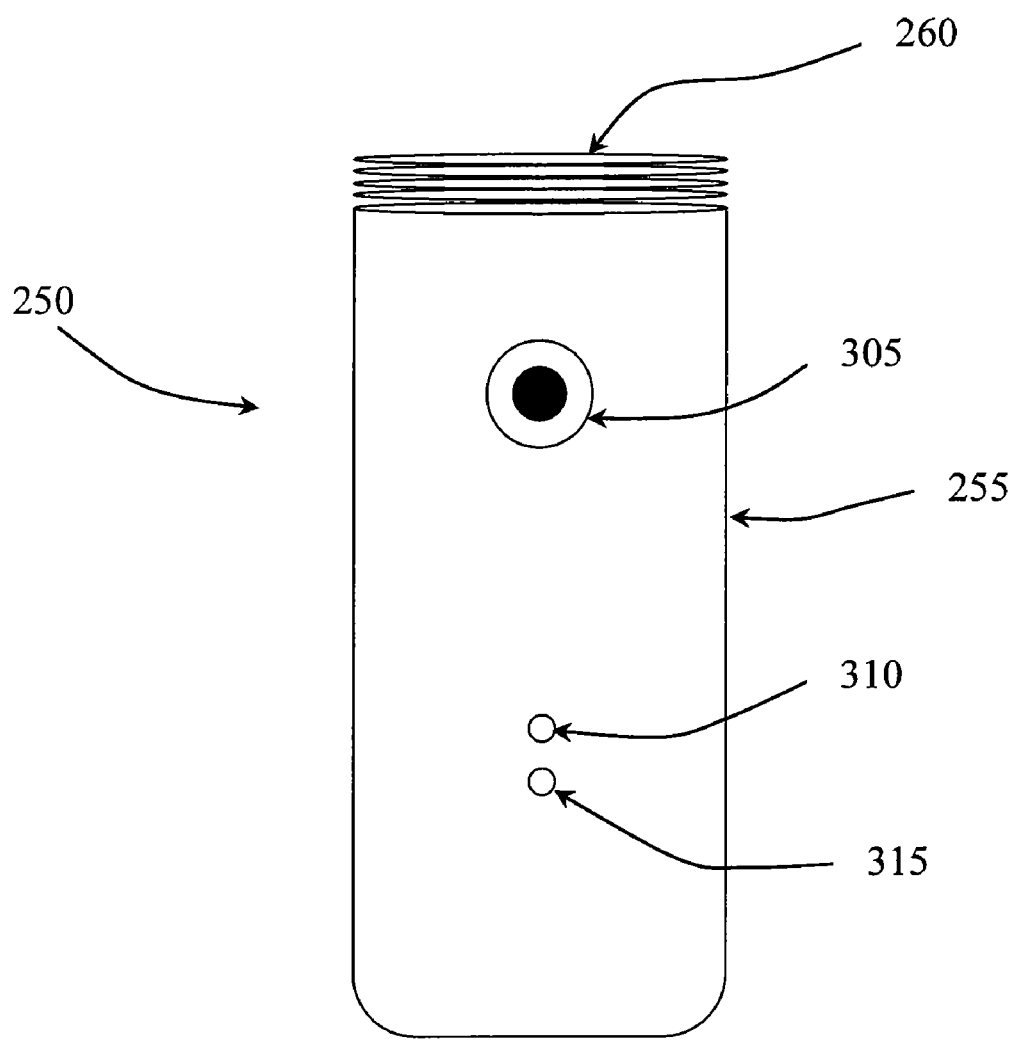
FIG. 3 is a front view of a limited reuse assembly for an ophthalmic hand piece according to an embodiment of the present invention.

FIG. 3 is a front view of a limited reuse assembly for an ophthalmic hand piece according to an embodiment of the present invention. In FIG. 3, limited reuse assembly 250 includes button 305, indicators 310, 315, housing 255, and threaded portion 260. Button 305 is located on housing 255 and provides an input to the system. For example, button 305 may be used to activate the system, the delivery of a drug, or other operation of the tip segment 205. Indicators 310, 315 are located on housing 255. In this embodiment, indicators 310, 315 are light emitting diodes that indicate a status of the system. For example, indicator 310 may illuminate when the substance to be delivered into the eye has been heated to a proper temperature range. Indicator 315 may illuminate when the substance has been delivered into the eye.

In another embodiment consistent with the principles of the present invention, a safety algorithm is implemented when the tip segment 205 is a drug delivery tip segment. The input device, such as button 305, that actuates the delivery of the drug, is disabled until the drug reaches the proper temperature range. In this manner, the delivery of the drug only occurs after the drug has reached the proper temperature range.

This safety algorithm can be implemented when the drug is contained in a phase-transition lipid. In such a case, the drug is contained in a substance that has a temperature-dependent viscosity. The substance and drug are heated so that the viscosity is suitable for delivery into an eye.

Figure 4:
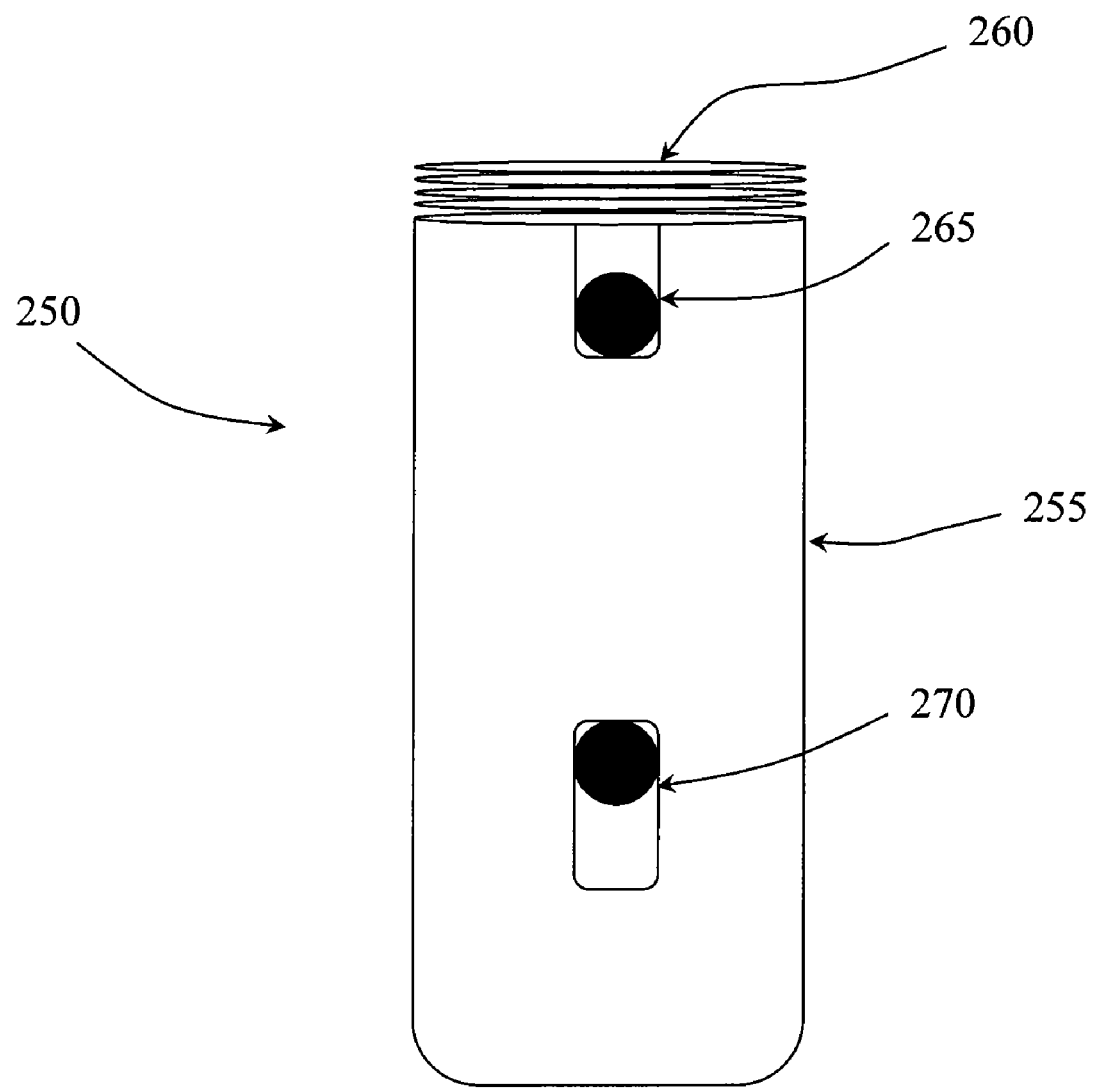
FIG. 4 is back view of a limited reuse assembly for an ophthalmic hand piece according to an embodiment of the present invention.

FIG. 4 is back view of a limited reuse assembly for an ophthalmic hand piece according to an embodiment of the present invention. The limited reuse assembly 250 includes a housing 255, a switch 270, a lock mechanism 265, and a threaded portion 260.

Figure 5:
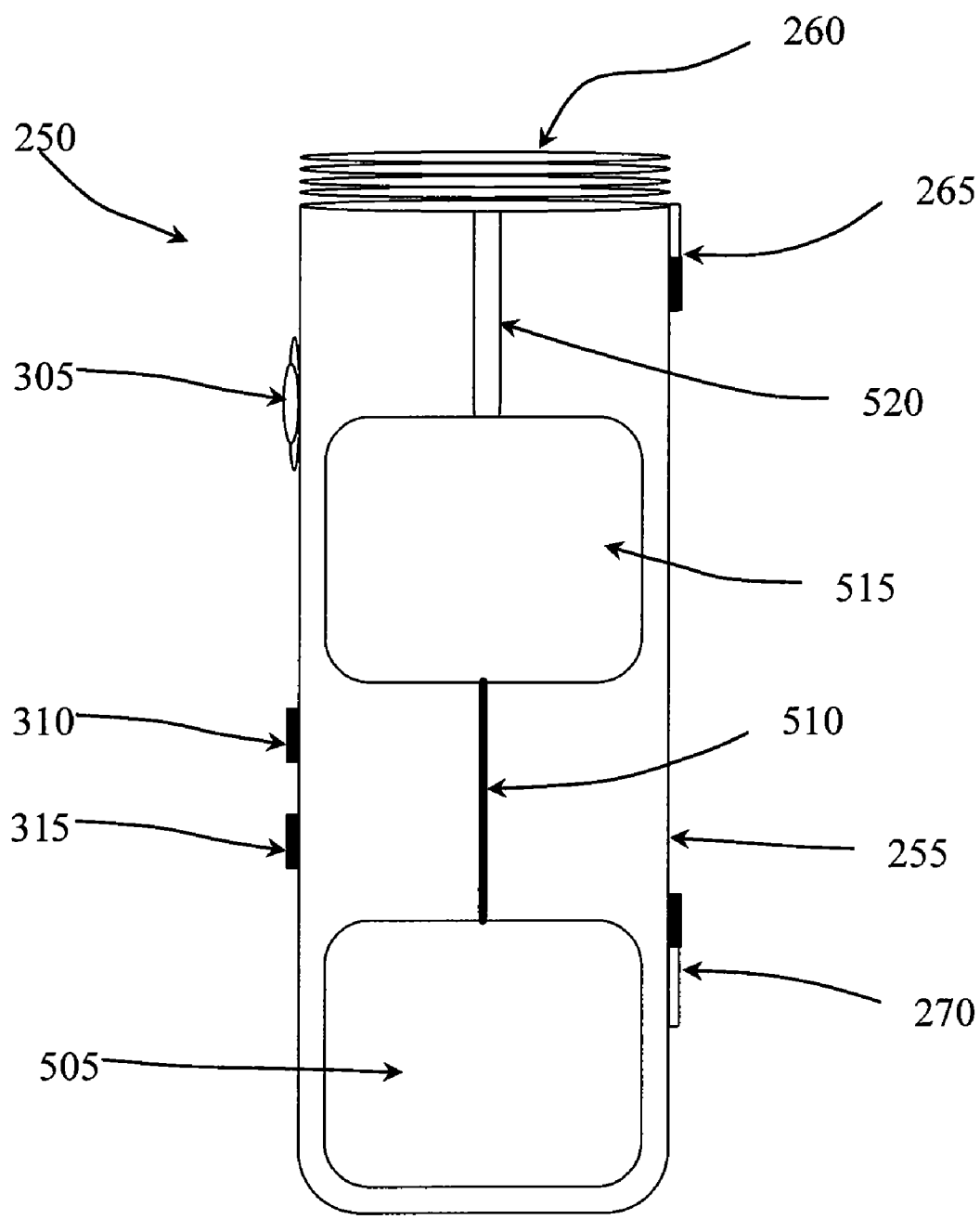
FIG. 5 is cross section view of a limited reuse assembly for an ophthalmic hand piece according to an embodiment of the present invention.

FIG. 5 is a cross section view of a limited reuse assembly for an ophthalmic hand piece according to an embodiment of the present invention. In FIG. 5, power source 505, interface 510, motor 515, and motor shaft 520 are located in housing 255. The top part of housing 255 has a threaded portion 260. Lock mechanism 265, switch 270, button 305, and indicators 310, 315 are all located on housing 255.

Power source 505 is typically a rechargeable battery, although other types of batteries may be employed. In addition, any other type of power cell is appropriate for power source 505. Power source 505 provides power to the system, and more particularly to motor 515. Power source 505 also provides power to a tip segment connected to limited reuse assembly 250. In such a case, power source 505 may provide power to a heater (not shown) located in the tip segment. Power source 505 can be removed from housing 255 through a door or other similar feature (not shown).

Interface 510 is typically an electrical conductor that allows power to flow from power source 505 to motor 515. Other interfaces, like interface 510, may also be present to provide power to other parts of the system.

Motor shaft 520 is connected to and driven by motor 515. Motor 515 is typically a stepper motor or other type of motor that is capable of moving motor shaft 520 precise distances. In one embodiment, motor shaft 520 is connected via a mechanical linkage to a tip segment that delivers a drug into an eye. In such a case, motor 515 is a stepper motor that can precisely move shaft 520 to deliver a precise quantity of drug into the eye. Motor 515 is secured to an interior surface of housing 255 by, for example, tabs that engage the outer surface of motor 515.

Lock mechanism 265, switch 270, and button 305 are all located on housing 255 so that they can be manipulated by hand. Likewise, indicators 310, 315 are located on housing 255 so that they can be viewed. Lock mechanism 265, switch 270, button 305, and indicators 310, 315 are also connected to a controller (not shown) via interfaces (not shown) located in housing 255.

Figure 6:
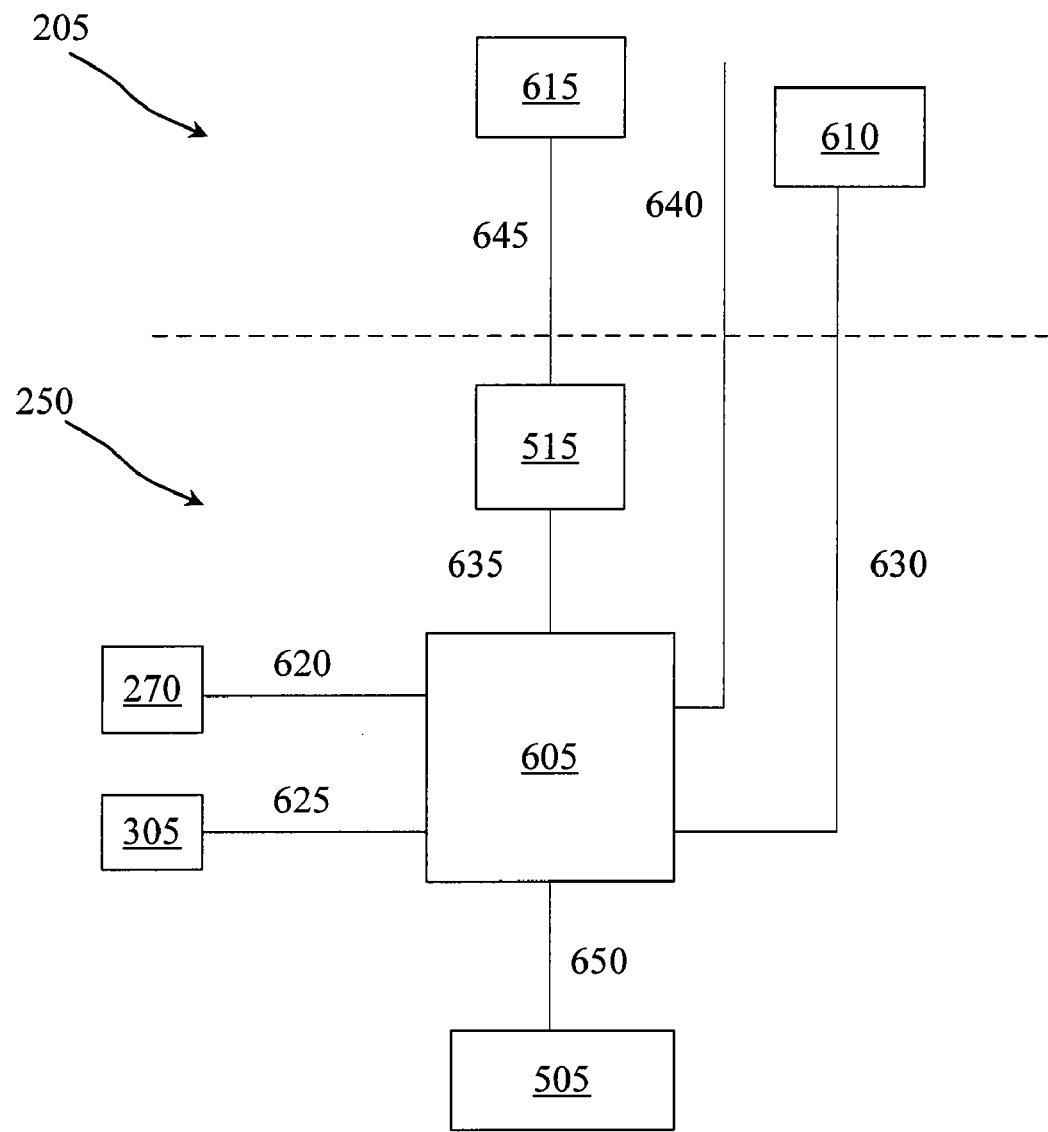
FIG. 6 is a block diagram of an ophthalmic hand piece including a drug delivery tip segment and a limited reuse assembly according to an embodiment of the present invention.

FIG. 6 is a block diagram of an ophthalmic hand piece including a drug delivery tip segment 205 and a limited reuse assembly 250 according to an embodiment of the present invention. The components contained in the tip segment 205 are located above the dotted line while the components contained in the limited reuse assembly 250 are located below the dotted line. In the block diagram of FIG. 6, tip segment 205 includes heater 610 and drug delivery device 615. Limited reuse assembly 250 includes power source 505, motor 515, controller 605, switch 270, button 305, and interfaces 620, 625, 630, and 650. Electrical interface 630, data interface 640, and mechanical interface 645 each form connections between tip segment 205 and limited reuse assembly 250.

In the embodiment of FIG. 6, controller 605 is connected to switch 270 via interface 620, to button 305 via interface 625, to power source 505 via interface 650, to motor 515 via interface 635, and to heater 610 via electrical interface 630. Data interface 640 connects controller 605 to tip segment 205. Motor 515 is connected to drug delivery device 615 via mechanical interface 645.

As noted with regard to FIG. 5, power source 505 is typically a rechargeable battery, although other types of batteries may be employed. In addition, any other type of power cell is appropriate for power source 505. In various embodiments of the present invention, power source 505 is a fuel cell, such as a methanol, water-based, or hydrogen fuel cell. In other embodiments, power source 505 is a lithium ion battery. Due to the compact nature of the hand piece, power source 505 is typically the size of one or two AA batteries. Such a size permits the application of many different battery and fuel cell technologies.

Controller 605 is typically an integrated circuit capable of performing logic functions. Controller 605 is typically in the form of a standard IC package with power, input, and output pins. In various embodiments, controller 605 is a motor controller, a heater controller, or a targeted device controller. In such a case, controller 605 performs specific control functions targeted to a specific device, such as a heater. For example, a heater controller has the basic functionality to control a heater, but may not have the functionality to control a motor. In other embodiments, controller 605 is a microprocessor. In such a case, controller 605 is programmable so that it can function to control different tip segments that perform different functions. In other cases, controller 605 is not a programmable microprocessor, but instead is a special purpose controller that is configured to control different tip segments that perform different functions.

Controller 605 also typically receives input data via data interface 640 and interfaces 620, 625. Data interface 640 carries data from the tip segment to controller 605. Such data may include a status of the tip segment or a component thereof. For example, data interface 640 may carry information about the type of tip segment connected to the limited reuse assembly, the dosage of a drug that is to be delivered into an eye, the status of the heater, the status of the drug delivery device, or other similar information about the system.

Interface 620 carries a signal from switch 270 to controller 605. This signal, for example, may activate the heater or activate the hand piece. Interface 625 carries a signal from button 305 to controller 605. This signal, for example, may activate the tip segment and initiate the delivery of a drug into they eye.

While shown as separate interfaces, data interface 640 and interfaces 620, 625, 635, 650 may all share a common interface line. Alternatively, any combination of these interfaces may share a common line. In such a case, one or more interface lines may carry signals from one or more different components of the system. For example, switch 270 and button 306 may share a single interface line that carries signals from both of them. These interfaces are typically made of an electrical conductor such as wire.

As noted above, motor 515 is typically a stepper motor, such as a variable reluctance motor, bipolar motor, unipolar motor, or bifilar motor. In other embodiments, motor 515 is any type of motor capable of moving its shaft finely or in small increments.

Drug delivery device 615 is driven by motor 515 via mechanical interface 645. In this embodiment, motor 515 provides a force that is transferred to drug delivery device 615 via a mechanical interface 645. Details of drug delivery device 615 are explained with reference to FIGS. 7-8 and 10-12.

Heater 610 is typically a resistive type heater. In one embodiment, heater 610 is a continuous wire with a resistance through which a current is passed. In other embodiments, heater 610 contains resistive elements connected in series through which a current is passed. The amount of current passed through heater 610 and the resistive characteristics of heater 610 are selected to provide the proper amount of heat.

Electrical connections (not shown) provide current to heater 610. These connections typically provide current to heater 610 from power source 505. In addition, a control line or electrical interface 630 provides signals that control the operation of heater 610. In this embodiment, a controller 605 receives temperature information from heater 610 and provides signals that control the operation of heater 610.

Figure 7:
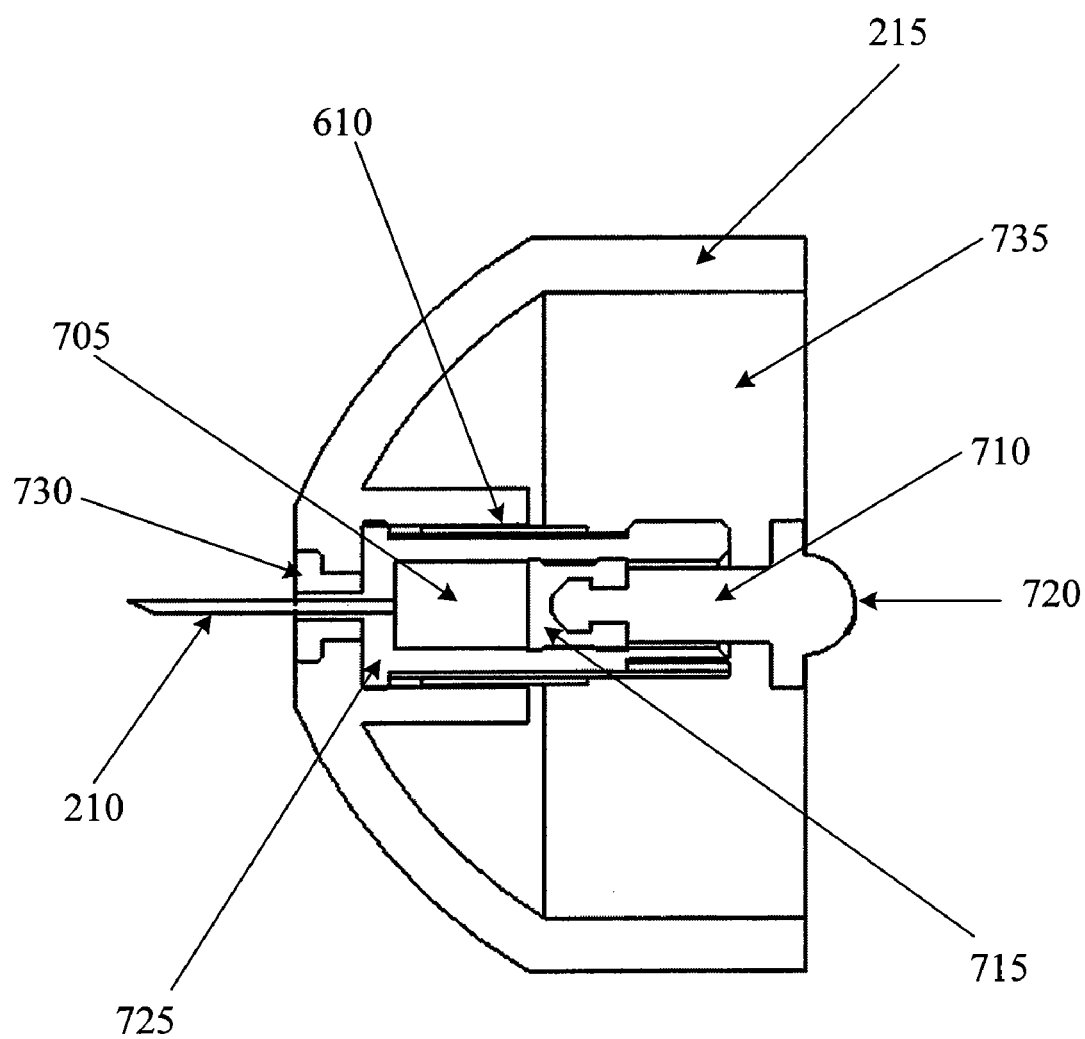
FIG. 7 is an exploded cross section view of a drug delivery tip segment for an ophthalmic hand piece according to an embodiment of the present invention.

FIG. 7 is an exploded cross section view of a drug delivery tip segment for an ophthalmic hand piece according to an embodiment of the present invention. In FIG. 7, the drug delivery tip segment includes a plunger limited reuse assembly 710, plunger tip 715, mechanical linkage interface 720, dispensing chamber 705, dispensing chamber housing 725, needle 210, heater 610, housing 215, support 735, and optional luer 730.

In the embodiment of FIG. 7, mechanical linkage interface is located on one end of plunger limited reuse assembly 710. Plunger tip 715 is located on the other end of plunger limited reuse assembly 710. Plunger limited reuse assembly 710 and plunger tip 715 collectively form a plunger. In this embodiment, mechanical linkage interface 720 is located on one end of the plunger. Dispensing chamber 705 is enclosed by dispensing chamber housing 725 and plunger tip 715. Needle 210 is fluidly coupled to dispensing chamber 705. In this manner, a substance located in dispensing chamber 725 can be contacted by plunger tip 715 and pushed out of needle 210. Needle 210 is secured to the drug delivery tip segment by optional luer 730. Heater 610 is located on dispensing chamber housing 725 and at least partially surrounds dispensing chamber 705. Support 735 holds the plunger (plunger limited reuse assembly 710 and plunger tip 715) and dispensing chamber housing 725 in place within housing 215. Housing 215 forms an outer skin on the drug delivery tip segment and at least partially encloses plunger limited reuse assembly 710, plunger tip 715, dispensing chamber 705, and dispensing chamber housing 725.

A substance to be delivered into an eye, typically a drug, is located in dispensing chamber 705. In this manner, the substance is contacted by the inner surface of dispensing chamber housing 725 and one face of plunger tip 715. Typically, dispensing chamber 705 is cylindrical in shape. Heater 610 is in thermal contact with dispensing chamber housing 725. In this manner, heater 610 is adapted to heat the contents of dispensing chamber 725. Current is applied to heater 610 through an electrical interface (not shown).

In one embodiment of the present invention, the substance located in dispensing chamber 705 is a drug that is preloaded into the dispensing chamber. In such a case, the drug delivery tip segment is appropriate as a single use consumable product. Such a disposable product can be assembled at a factory with a dosage of a drug installed. A precise volume of a substance can be preloaded into the delivery device. This helps to prevent dosing error on the part of the medical professional.

Additionally, proper storage and handling of the drug can be more easily assured. Since the drug is loaded into the system at the factory, the drug can be stored under precise conditions. Shipment of a preloaded system can also be accomplished under precise conditions.

When the drug is preloaded into dispensing chamber 705, a set quantity of the drug can be preloaded. For example, 100 microliters of a drug can be loaded into dispensing chamber 705, and any quantity up to 100 microliters can be dispensed. In such a case, the plunger (plunger limited reuse assembly 710 and plunger tip 715) can be moved a precise distance to deliver a precise dosage of drug from the dispensing chamber 705, through the needle 210, and into an eye. This provides for flexibility of dosing and for ease of assembly.

In operation, the drug delivery tip segment of FIG. 7 is attached to a limited reuse assembly (not shown). Mechanical interface 720 mates with a mechanical interface on the limited reuse assembly. When a force is applied to plunger limited reuse assembly 710, plunger tip 715 is displaced. The displacement of plunger tip 715 in turn displaces the substance contained in dispensing chamber 705. The substance is pushed out of needle 210.

Figure 8:
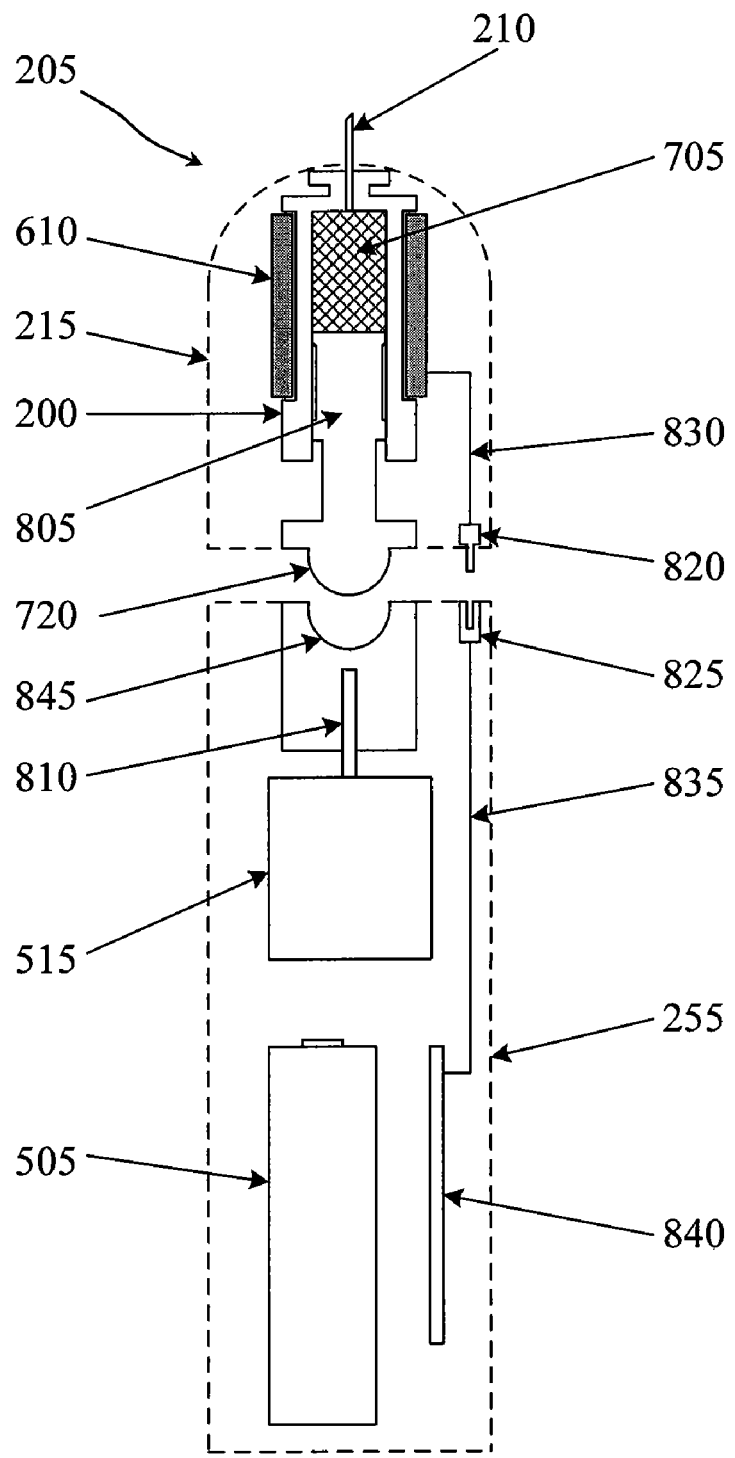
FIG. 8 is cross section view of a drug delivery tip segment and a limited reuse assembly according to an embodiment of the present invention.

FIG. 8 is cross section view of a drug delivery tip segment and a limited reuse assembly according to an embodiment of the present invention. FIG. 8 shows how tip segment 205 interfaces with limited reuse assembly 250. In the embodiment of FIG. 8, tip segment 205 includes mechanical linkage interface 720, plunger 805, dispensing chambering housing 725, tip segment housing 215, heater 610, needle 210, dispensing chamber 705, interface 830, and tip interface connector 820. Limited reuse assembly 250 includes mechanical linkage 845, motor shaft 810, motor 515, power source 505, controller 840, limited reuse assembly housing 255, interface 835, and limited reuse assembly interface connector 825.

In tip segment 205 mechanical linkage 720 is located on one end of plunger 805. The other end of plunger 805 forms one end of dispensing chamber 705. Plunger 805 is adapted to move slidably within dispensing chamber 705. An outer surface of plunger 805 is fluidly sealed to an inner surface of dispensing chamber housing 725. Dispensing chamber housing 725 surrounds the dispensing chamber 705. Typically, dispensing chamber housing 725 has a cylindrical shape. As such, dispensing chamber 705 also has a cylindrical shape.

Needle 210 is fluidly coupled to dispending chamber 705. In such a case, a substance contained in dispending chamber 705 can pass through needle 210 and into an eye. Heater 610 at least partially surrounds dispensing chamber housing 725. In this case, heater 610 is adapted to heat dispensing chamber housing 725 and any substance contained in dispending chamber 705. In other words, heater 610 is in thermal contact with dispensing chamber housing 725. Interface 830 connects heater 610 with tip interface connector 820.

The components of tip segments of 205, including dispensing chamber housing 725, heater 610, and plunger 805 are at least partially enclosed by tip segment housing 215. In one embodiment consistent with the principles of the present invention, a seal is present on a bottom surface of tip segment housing 215. In this manner, plunger 805 is sealed to tip segment housing 215. This seal prevents contamination of any substance contained in dispensing chamber 705. For medical purposes, such a seal is desirable. This seal can be located at any point on plunger 805 or on dispensing chamber housing 725. In such a case tip segment housing 215 maybe connected to dispensing chamber housing 725 to form an air tight or fluid tight seal. In another embodiment, tip segment housing 215 maybe sealed to plunger 805 near the end on which mechanical linkage interface 720 resides. In such a case, an air tight or fluid tight seal may be formed between a location on plunger 805 and tip segment housing 215.

In addition, tip segment 205 may contain a plunger stop mechanism. As shown in FIG. 8, the bottom portion of plunger 805 (the portion on which mechanical linkage interface 720 resides) is adapted to contact the bottom portion of dispensing chamber housing 725. In such a case, as plunger 805 advances upward toward needle 210, mechanical linkage interface 720 also advances upward toward needle 210. A top surface of mechanical linkage interface 720 contacts a bottom surface of dispensing chamber housing 725. In this embodiment, the protrusions on the bottom end on plunger 805 and the bottom surface of dispensing chamber housing 725 form a plunger stop mechanism. Plunger 805 can not be advanced any further than the point at which the top surface of mechanical linkage interface 720 contacts the bottom surface of dispensing chamber housing 805. Such a plunger stop mechanism can provide a safety feature, such as to prevent plunger 805 from contacting needle 210 and possibly dislodging it. In another embodiment consistent with the principles of the present invention, such a plunger stop mechanism may also include a locking mechanism so that plunger 805 cannot be retracted or moved away from needle 210 when needle 210 is removed from the eye. Such a plunger lock mechanism helps to prevent reflux of the substance when needle 210 is removed.

In limited reuse assembly 250, power source 505 provides power to motor 515. An interface (not shown) between power source 505 and motor 515 serves as a conduit for providing power to motor 515. Motor 515 is connected to motor shaft 810. When motor 515 is a stepper motor, motor shaft 810 is integral with motor 515. Mechanical linkage interface 845 is connected to motor shaft 810. In this configuration, as motor 515 moves motor shaft 810 upward toward needle 210 mechanical linkage 845 also moves upward toward needle 210.

Controller 840 is connected via interface 835 to limited reuse assembly interface connector 825. Limited reuse assembly interface connector 825 is located on a top surface of limited reuse assembly housing 255 adjacent to mechanical linkage interface 845. In this manner, both limited reuse assembly interface connector 825 and mechanical linkage interface 845 are adapted to be connected with tip interface connector 820 and mechanical linkage interface 720 respectively.

Controller 840 and motor 515 are connected by an interface (not shown). This interface (not shown) allows controller 840 to control the operation of motor 515. In addition, an optional interface (not shown) between power source 505 and controller 840 allows controller 840 to control operation of power source of 505. In such a case, controller 840 may control the charging and the discharging of power source 505 when power source 505 is a rechargeable battery.

Tip segment 205 is adapted to mate with or attach to limited reuse assembly 250. In the embodiment of FIG. 8, mechanical linkage interface 720 located on a bottom surface of plunger 805 is adapted to connect with mechanical linkage interface 845 located near a top surface of limited reuse assembly housing 255. In addition, tip interface connector 820 is adapted to connect with limited reuse assembly interface connector 825. When tip segment 205 is connected to limited reuse assembly 250 in this manner, motor 515 and motor shaft 810 are adapted to drive plunger 805 upward toward needle 210. In addition, an interface is formed between controller 840 and heater 610. A signal can pass from controller 840 to heater 610 through interface 835, limited reuse assembly interface connector 825, tip interface connector 820, and interface 830. Likewise a signal can pass from heater 610 to controller 840 through interface 830, tip interface connector 820, limited reuse assembly interface connector 825, and interface 835. In this manner, controller 840 is adapted to control the operation of heater 610.

In operation, when tip segment 205 is connected to limited reuse assembly 250, controller 840 controls the operation of motor 515. Motor 515 is actuated and motor shaft 810 is moved upward toward needle 210. In turn, mechanical linkage interface 845, which is connected to mechanical linkage interface 720, moves plunger 805 upward toward needle 210. A substance located in dispensing chamber 705 is then expelled through needle 210.

In addition, controller 840 controls the operation of heater 610. Heater 610 is adapted to heat an outside surface of dispensing chamber housing 725. Since dispensing chamber housing 725 is at least partially thermally conductive, heating dispensing chamber housing 725 heats a substance located in dispensing chamber 705. Temperature information can be transferred from heater 610 through interface 830, tip interface connector 820, limited reuse assembly interface connector 825, and interface 835 back to controller 840. This temperature information can be used to control the operation of heater 610. Typically, controller 840 controls the amount of current that is sent to heater 610. The more current sent to heater 610, the hotter it gets. In such a manner, controller 840 can use a feed back loop comprising information about the temperature of heater 610 to control the operation of heater 610. Any suitable type of control algorithm, such as a proportional integral derivative algorithm, can be used to control the operation of heater 610.

Figure 9:
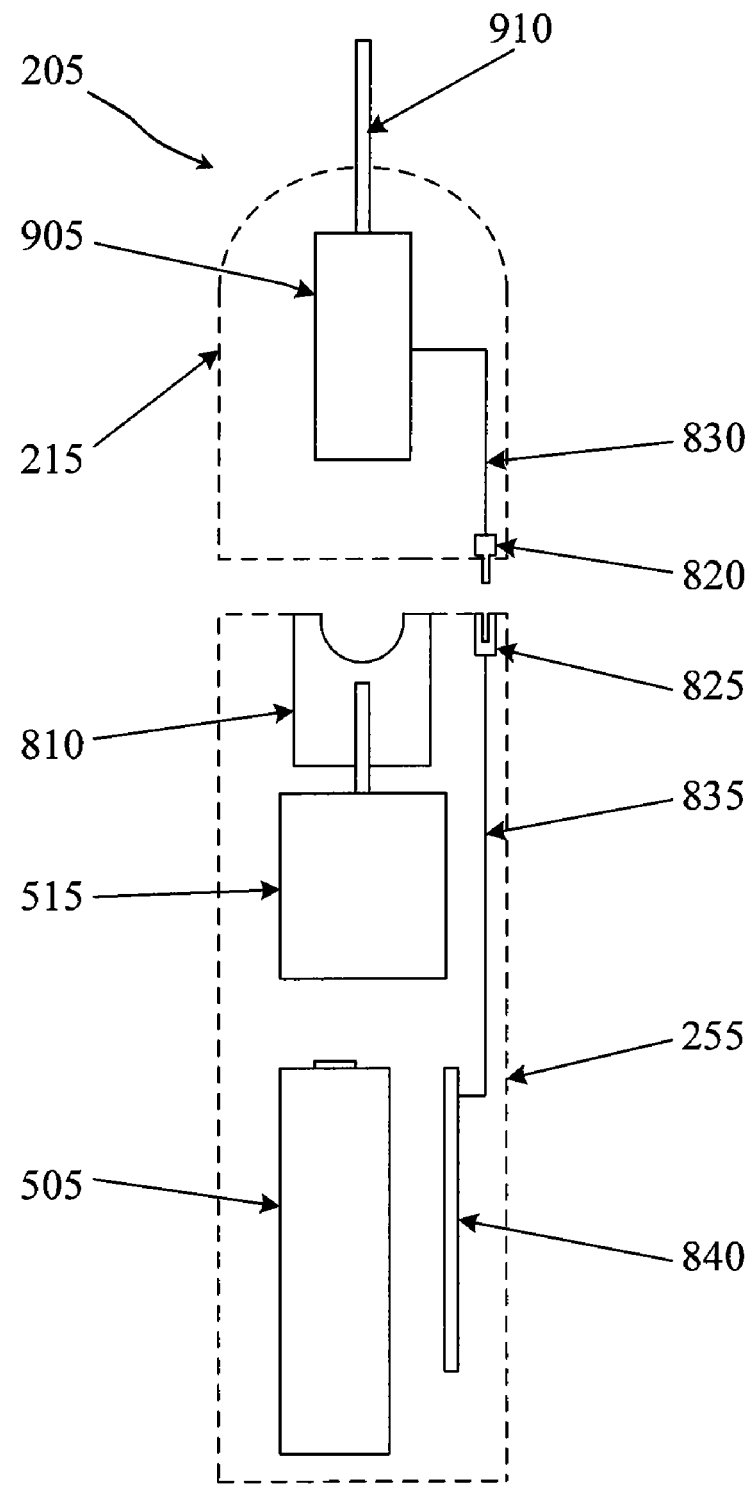
FIG. 9 is cross section view of a cauterizing tip segment and a limited reuse assembly according to an embodiment of the present invention.

FIG. 9 is a cross section view of a cauterizing tip segment and a limited reuse assembly according to an embodiment of the present invention. In FIG. 9, limited reuse assembly 250 is substantially the same as the limited reuse assembly 250 shown in FIG. 8. Tip segment 200, however, is a cauterizing tip rather than a drug delivery tip.

Tip segment 205 includes cauterizing driver 905, tip segment housing 215, cauterizing tip 910, interface 830, and tip interface connector 820. Cauterizing driver 905 is connected to cauterizing tip 910 and is adapted to operate cauterizing tip 910. Cauterizing driver 905 is connected to interface 830 which in turn is connected to tip interface connector 820.

Cauterizing tip segment 900 is adapted to interface with and connect to limited reuse assembly 250. In one embodiment consist with the principles of the present invention, cauterizing tip segment 900 and limited reuse assembly 250 can be screwed together via two threaded segments (not shown). Tip interface connector 820 is also adapted to interface with and connect to limited reuse assembly connector interface 825.

When cauterizing tip segment 900 is connected to limited reuse assembly 250, controller 840 is connected to cauterizing driver 905 via interface 835, limited reuse assembly interface connector 825, tip interface connector 820 and interface 830. In such a case, controller 840 can controller the operation of cauterizing driver 905. For example, controller 840 can control the temperature at which cauterizing tip 910 is maintained by cauterizing driver 905. In addition, signals passing between controller 840 and cauterizing driver 905 can serve to provide controller 840 with feedback information about the temperature of cauterizing tip 910. Typically, cauterizing driver 905 and cauterizing tip 910 are heating devices designed to cauterize blood vessels. Cauterizing tip 910 is usually a small diameter wire. Such a small diameter wire can be easily inserted into the eye during surgery to cauterize blood vessels.

In the configuration of FIG. 9, limited reuse assembly 250 is a universal limited reuse assembly. In such a case, limited reuse assembly 250 can be connected to at least two different types of tip segments, such as tip segment 205 and cauterizing tip segment 900. Limited reuse assembly 250 can operate either a drug delivery tip segment or a cauterizing tip segment. In addition, limited reuse assembly 250 may be able to operate other types of tip segments that perform different functions. Such a universal limited reuse assembly provides streamlined operation as only one limited reuse assembly is required to operate multiple different tip segments. In addition, a single limited reuse assembly 250 maybe manufactured and bundled with different tip segments.

Figure 10:
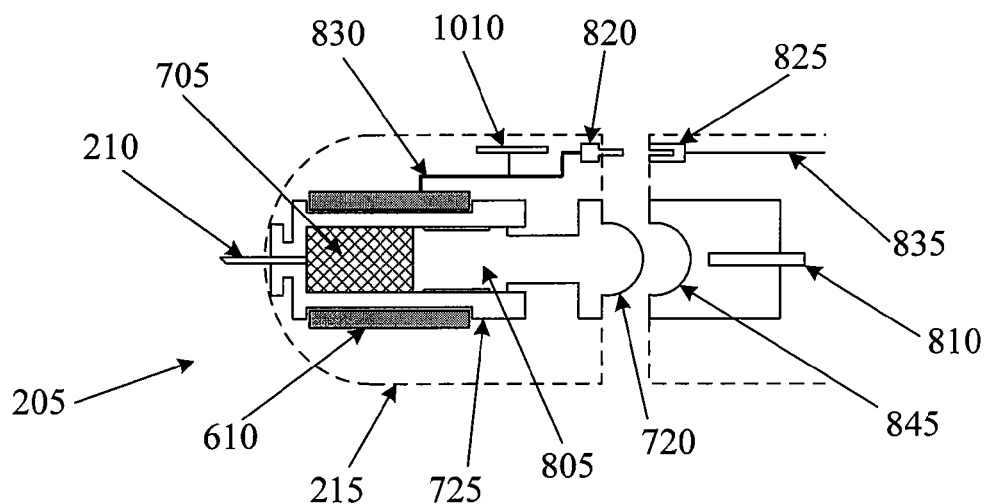
FIG. 10 is cross section view of a drug delivery tip segment and a partial cross section view of a limited reuse assembly according to an embodiment of the present invention.

FIG. 10 is a cross section view of a drug delivery tip segment and a partial cross section view of a limited reuse assembly according to an embodiment of the present invention. In FIG. 10, tip segment 205 includes mechanical linkage interface 720, plunger 805, dispensing chamber housing 725, tip segment housing 215, heater 610, needle 210, dispensing chamber 705, interface 830, data store 1010, and tip interface connector 820. The embodiment of tip segment 205 shown in FIG. 10 is similar to the embodiment of tip segment 205 shown in FIG. 8 with the exception that tip segment 205 of FIG. 10 includes a data store 1010. Tip segment 205 of FIG. 10 operates in the same manner as tip segment 205 of FIG. 8.

Limited reuse assembly interface connector 825, interface 835, mechanical linkage interface 845, and motor shaft 810 are shown in the partial rendering of the limited reuse assembly. These components operate in the same manner as described with reference to limited reuse assembly 250 in FIG. 8.

Data store 1010 is connected to interface 830 in tip segment 205. Data store 1010 is typically a semiconductor memory such as an EEPROM. Data store 1010 is configured to store identifying information about tip segment 205. In addition, data store 1010 may also store dosage information for a drug contained in dispensing chamber 705.

In the embodiment of FIG. 10, interface 830, tip interface connector 820, limited reuse assembly interface 825, and interface 835 all form a data interface between tip segment 205 and limited reuse assembly 250. In this manner, information from heater 610 maybe passed back to limited reuse assembly 250 via this series of interfaces and interface connectors. In addition, data stored on data store 1010 may also be read by controller (not shown) via this series of interfaces and interface connectors. When tip segment 205 is connected to limited reuse assembly 250, mechanical linkage interface 845 is connected to mechanical linkage interface 720 and tip interface connector 820 is connected to limited reuse assembly interface connector 825. The connection of tip interface connector 820 to limited reuse assembly interface connector 825 allows the transfer of information or data from heater 610 and data store 1010 to controller 840.

In one embodiment consistent with the principle of the present invention, information about a type of tip segment is stored on data store 1010. This information relates to whether tip segment 205 is a drug delivery tip segment, a cauterizing tip segment, or any other type of tip segment. This identifier information stored on data store 1010 can be read by controller 840. In such a case, controller 840 uses this information to determine the proper operation of tip segment 205. For example, if tip segment 205 is a drug delivery tip segment or a drug delivery device, then controller 840 can use the proper algorithm to control tip segment 205. Likewise, when a cauterizing tip segment, such as cauterizing tip segment 900, is attached to limited reuse assembly 250, information stored on data 1010 can be used by controller 840 to control the operation of the cauterizing tip.

In addition to identifier information, data store 1010 may also contain dosage information. When tip segment 205 is a drug delivery tip segment, information about a proper drug dosage for a drug contained in dispensing chamber 705 maybe contained on data store 1010. In such a case, controller 840 can read the dosage information from data store 1010 and operate motor 515 in a manner suitable to deliver the proper dosage. For example, 100 microliters may be contained dispensing chamber 705. Information stating that a dosage of 20 microliters is to be delivered into an eye maybe stored on data store 1010. In such a case, controller 840 reads the dosage information (that 20 microliters should be delivered into the eye) from data store 1010. Controller 840 can then operate motor 515 to deliver the 20 microliter dosage. Controller 840 can cause motor 515 to move motor shaft 810 and mechanical linkage 845 a set distance related to a dosage of 20 microliters. In such a case, plunger 805 is moved this set distance so that only 20 micro liters of a drug is expelled from needle 210 and into an eye.

In one embodiment consistent with the principles of the present invention, controller 840 has various plunger distances stored on it. Each of these plunger distances is related to a different dosage. For example, one plunger distance maybe associated with a dosage of 20 microliters and a second larger plunger distance maybe associated with a dosage of 40 microliters. In this manner controller 840 can use the set plunger distance to control motor 515, motor shaft 810, mechanical linkage interface 845, and mechanical linkage interface 720 to move plunger 805 this set distance. In other words, controller 840 uses a distance that plunger 805 must travel to deliver a given dosage of drug. Since motor shaft 810 and mechanical linkage interface 845 are connected to mechanical linkage interface 720, a movement of motor shaft 810 produces a corresponding movement of plunger 805. When motor 515 is a stepper motor, controller 840 controls the movement of motor 515 such that plunger 805 is moved the proper distance to deliver the required dosage from dispensing chamber 705, through needle 210, and into an eye.

In another embodiment consistent with the principles of the present invention, controller 840 may calculate a distance that plunger 805 must be moved to deliver the desired dosage. For example, if dosage information corresponding to a drug dosage of 20 microliters is read from data store 1010 by controller 840, then controller 840 may use this information to calculate a proper distance that plunger 805 must be moved. Since the volume of dispensing chamber 705 as well as the volume of a drug loaded in dispensing chamber 705 is known, a distance that plunger 805 must be moved to deliver that required dosage can be calculated by controller 840. When dispensing chamber 705 has a cylindrical shape, the volume of the dispensing chamber can be calculated by using the cross section area of the cylinder (the area of a circle) times the height of the dispensing chamber. This simple mathematical formula can be used to calculate the total volume of the dispensing chamber 705. Since the cross section area of dispensing chamber 705 is constant for any given application, the height which corresponds to a distance that plunger 805 travels can be calculated for any dosage amount.

For example, assume that 100 microliters of a drug is loaded into dispensing chamber 705 and that the cross section area of dispensing chamber 705 is 10. When dispensing chamber 705 is in the shape of a cylinder, the height of that cylinder is also 10. To deliver a dosage of 20 microliters which corresponds to 20% of the total volume of dispensing chamber 705, it is necessary to move plunger 805 upward toward needle 210 a distance of 2. In other words, a dosage of 20 microliters corresponds to 20% of the total volume of dispensing chamber 705. In such a case, plunger 805 should be moved upward toward needle 210 a distance equal to 20% of the total height of dispensing chamber 705. Controller 840 can then control motor 515 such that motor shaft 810 moves drives plunger 805 upward a distance of 20% of the total height of dispensing chamber 705.

In addition, controller 840 may read information about a rate at which plunger 805 should be moved in order to properly deliver a dosage of drug. In such a case, controller 840 reads information about the rate of drug delivery from data store 1010 and uses that information to operate motor 515 to drive plunger 805 at that rate. The rate at which plunger 805 moves may be fixed or variable. In some applications, it may be desirable to move plunger 805 faster than in other applications. For example, when the drug contained in dispensing 705 is a drug that should be heated before being injected into an eye, it maybe desirable to drive plunger 805 at a rate such that the heated drug does not cool and clog needle 210. In other applications, it maybe desirable to move plunger 805 slowly in order to improve the delivery of a drug contained in dispensing chamber 705.

While information about a dosage amount and a dosage rate have been described as being stored on data 1010, data store 1010 may also include any other type of information related to delivery of a drug. For example, data store 1010 may include information about the type of drug contained in dispensing chamber 705, various characteristics of that drug, or other characteristics of a proper dosage or a proper delivery of that drug. In addition, data store 1010 may contain safety information, information about the proper operation of tip segment 205, or any other information related to the tip segment or limited reuse assembly.

In another embodiment consistent with the principles of the present invention, a dosage maybe selectable by the medical professional who is administering the drug. In such a case, an input device (not shown) located on limited reuse assembly 250 or on tip segment 205 may enable a doctor to select the desired drug dosage. In such a case, controller 840 receives the desired drug dosage and operates motor 515 to move plunger 805 the required distance to deliver the desired dosage. Such a user selectable dosage scheme may be implemented simply by adding an extra input device.

It may be desirable to include dosage information on data store 1010 so that a dosing error is less likely to occur. In such a case, a number of different drug delivery tip segments 205 maybe manufactured and loaded with a drug at the factory. Dosage information can also be loaded onto data store 1010 at the factory. In such a case, a number of different tip segments each with the same amount of drug contained in the dispensing chamber 705 but with different dosage information stored on data store 1010 can be manufactured and shipped. A doctor can then order the tip segment 205 with the required dosage information on the data store 1010. Packaging can be clearly labeled to identify the dosage information so that the proper dosage is administered to a patient.

Figure 11:
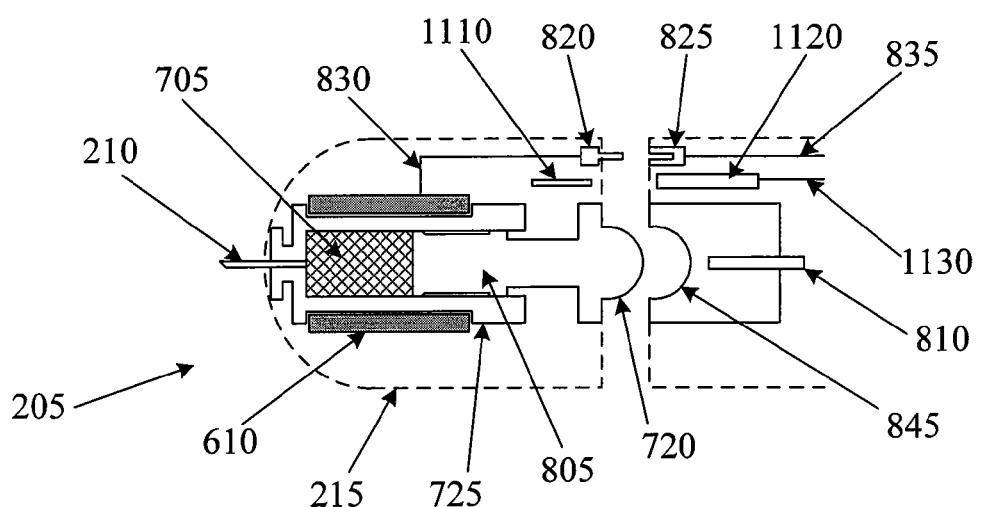
FIG. 11 is cross section view of a drug delivery tip segment and a partial cross section view of a limited reuse assembly according to an embodiment of the present invention.

FIG. 11 is a cross section view of a drug delivery tip segment and a partial cross section view of a limited reuse assembly according to an embodiment of the present invention. In FIG. 11, tip segment 205 includes a radio frequency identification tag 1110. In all other respects, tip segment 205 of FIG. 11 is identical to tip segment 205 of FIG. 8. The various components and the operation of the various components of tip segment 205 of FIG. 8 are the same as tip segment 205 of FIG. 11.

The partial view of limited reuse assembly 250 depicted in FIG. 11 also includes a radio frequency identification (FRID) reader 1120 and RFID interface 1130. In all other respects, limited reuse assembly 250 of FIG. 11 is the same as limited reuse assembly 250 of FIG. 8. RFID interface 1130 is connected to controller 840 (not shown).

RFID tag 1110 is configured to hold the same type of information that data store 1010 holds with respect to FIG. 10. In this manner, RFID tag 1110 is simply another type of data store 1010. However, as is commonly know, RFID tag 1110 does not require a wired connection to RFID reader 1120. In this manner, a wireless connection between RFID tag 1110 and RFID reader 1120 can be established.

The RFID reader 1130 of an RFID system (which includes RFID tag 1110, RFID reader 1120, and RFID interface 1130) is contained near the top of limited reuse assembly 250. RFID reader 1120 is located adjacent to mechanical linkage interface 845 near a top surface of limited reuse assembly housing 255. RFID reader 1120 is designed to read information from RFID tag 1110.

In one type of RFID system, a passive RFID system, RFID tag 1110 does not have a power supply. Instead, the passive RFID tag relies on the electromagnetic field produced by the RFID reader 1120 for its power. The electromagnetic field produced by the RFID reader 1120 and emitted from the RFID reader antenna (not shown) induces a small electrical current in RFID tag 1110. This small electrical current allows RFID tag 1110 to operate. In this passive system the RFID tag is designed to collect power from both the electromagnetic field produced by the RFID reader 1120 and emitted by the RFID reader 1120 and to transmit an outbound signal that is received by the RFID reader 1120.

In operation the RFID reader antenna (not shown) transmits a signal produced by the RFID reader 1120. The RFID tag antenna (not shown) receives this signal and a small current is induced in the RFID tag 1110. This small current powers the RFID tag 1110. RFID tag 1110 can then transmit a signal through its RFID tag antenna to RFID reader antenna and the RFID reader 1120 itself. In this manner, the RFID tag 1110 and the RFID read 1120 can communicate with each over a radio frequency link. RFID tag 1110 transmits information, such as dosage information or tip segment information, through RFID tag antenna to RFID reader 1120. This information is received by RFID reader 1120. In this manner, information can be transferred from the tip segment 205 to the limited reuse assembly 250. The RFID reader 1120 can transmit information to the RFID tag 1110 in a similar fashion. For example, RFID reader 1120 can transmit information such as dosage information over the radio frequency signal emitted by RFID reader 1120. RFID tag 1120 receives this radio frequency signal with the information. RFID tag 1110 can then store this information.

While the present invention is described as having an RFID system, any other type of wireless system can be used to transfer information between limited reuse assembly 250 and tip segment 205. For example a Bluetooth protocol maybe used to establish a communication link between limited reuse assembly 250 and tip segment 205. Information can then be transferred between limited reuse assembly 250 and tip segment 205 over this communication link. Other embodiments used to transfer information include an infrared protocol, 802.11, fire wire, or other wireless protocol.

The operation of tip segment 205 of FIG. 11 is similar to the operation of tip segment 205 of FIG. 10. The difference between the embodiment of FIG. 10 and the embodiment of FIG. 11 is that the embodiment of FIG. 11 uses an RFID system rather than a wired data store system to transfer information to tip segment 205 to limited reuse assembly 250.

In the embodiment of FIG. 11, interface 830, tip interface connector 820, limited reuse assembly interface connector 825, and interface 835 form an electrical interface. In this case, this series of interfaces and interface connectors carries power to heater 610. In other embodiments of the present invention, this series of interface and interface connectors can operate both as a data interface and a power interface.

Figure 12:
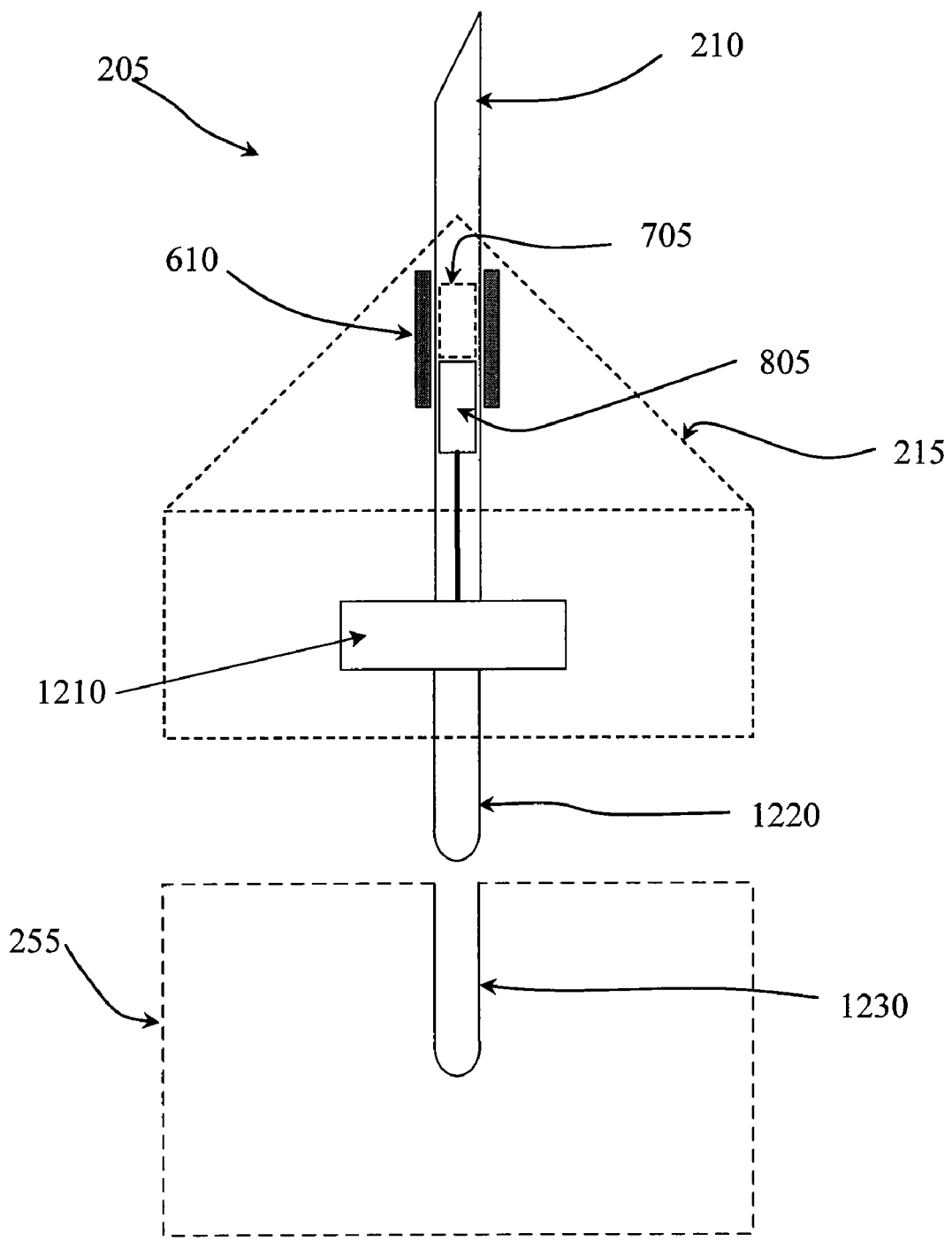
FIG. 12 is cross section view of a drug delivery tip segment and a partial cross section view of a limited reuse assembly according to an embodiment of the present invention.

FIG. 12 is a cross section view of a drug delivery tip segment and a partial cross section view of a limited reuse assembly according to an embodiment of the present invention. In FIG. 12, tip segment 205 includes motor 1210, heater 610, needle 210, substance 1215, plunger 805, tip segment housing 215, and shaft 1220. Limited reuse assembly 250 includes limited reuse assembly housing 255 and shaft hold 1230.

In the embodiment of FIG. 12, motor 1210 is contained in tip segment 205 and not in limited reuse assembly 250. Shaft 1220 is connected to motor 1210. Motor 1210 is connected to plunger 805. Substance 1215 is located within needle 210 above the upper surface of plunger 805. Heater 610 surrounds needle 210 in the vicinity of substance 215. Motor 1210, plunger 805, and heater 610 are all at least partially enclosed in tip segment housing 215.

Shaft hold 1230 is included in limited reuse assembly housing 255. Shaft hold 1230 operates to interface with shaft 1220 when tip segment 205 and limited reuse assembly 250 are connected together.

In operation, tip segment 205 is connected to limited reuse assembly 250. Shaft 1220 is inserted into shaft hold 1230 and tip segment 205 is fastened to limited reuse assembly 250. In such, a case tip segment housing 215 is attached to limited reuse assembly housing to 255.

A controller (not shown) contained within limited reuse assembly housing 255 operates motor 1210 contained within tip segment housing 215. The operation of the drug delivery tip segment 205 of FIG. 12 is similar to that described with respect to the drug delivery tip segment 205 of FIG. 8.

In FIG. 12, motor 1210 is contained within tip segment 205. When tip segment 205 is disposable, motor 1210 must also be discarded along with tip segment 205. Motor 1210 contained in tip segment housing 215 may also allow for a better seal so that substance 1215 contained in needle 210 is not contaminated.

Figure 13:
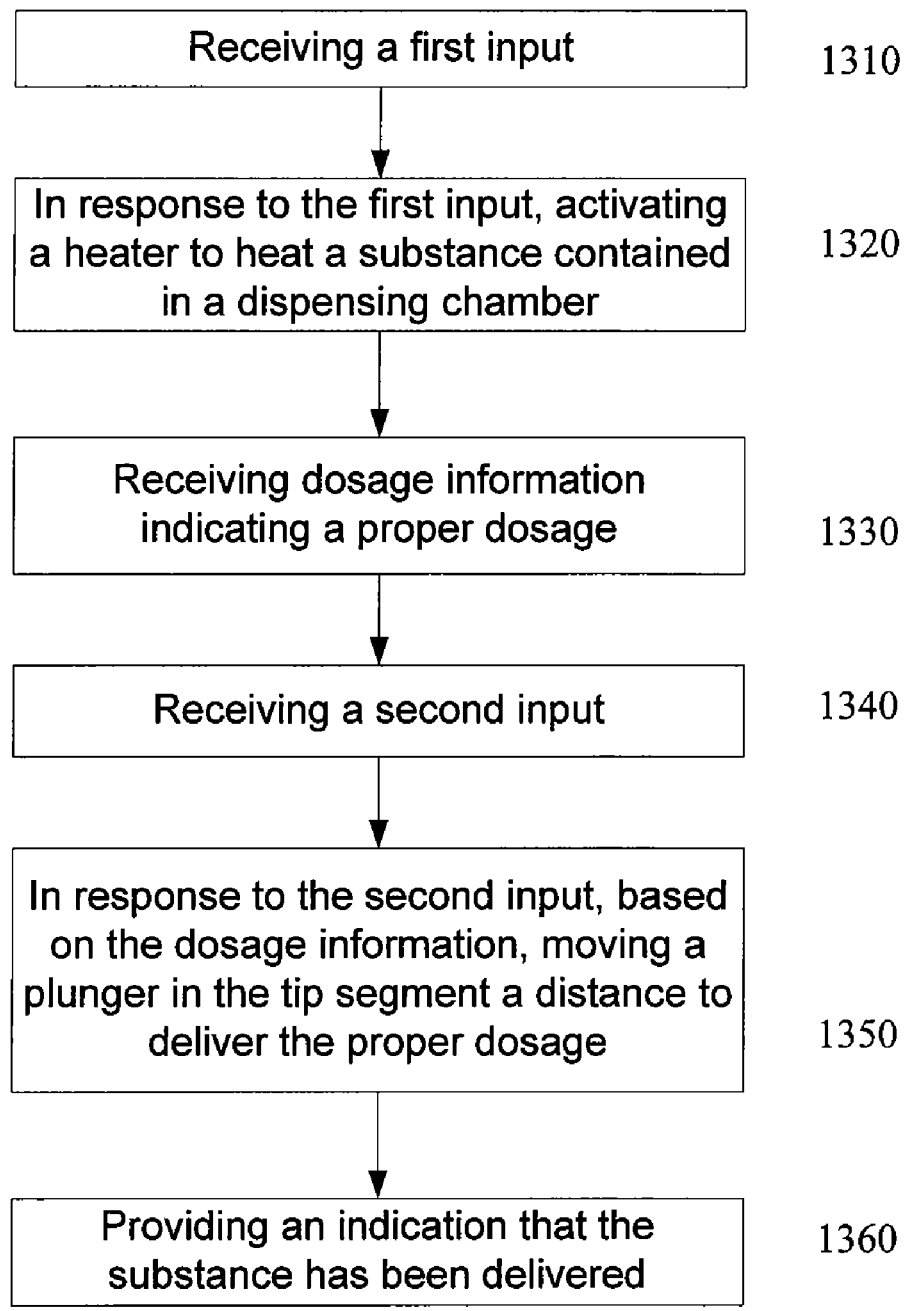
FIG. 13 is a block diagram of a method of operating a drug delivery hand piece according to an embodiment of the present invention.

FIG. 13 is a block diagram of a method of operating a drug delivery hand piece according to an embodiment of the present invention. In 1310, a first input is received. Typically, this first input is generated via a switch or button located on the hand piece. For example, a surgeon may activate a switch to turn the heater on. In response to this first input, in 1320, a heater is activated to heat a substance contained in a dispensing chamber. Typically, current is provided to the heater and controlled by the controller.

In 1330, dosage information is received. This dosage information is typically received by the controller so that the controller can control the operation of the hand piece to deliver the required dosage. The dosage information may be located in the tip segment itself (on a memory or RFID tag as previously described). In such a case, the dosage information is transferred from the tip segment to the limited reuse assembly.

In 1340, a second input is received. Typically, this second input is generated via a switch or button located on the hand piece. For example, a surgeon may press a button to begin the delivery of the substance. In response to this second input and based on the dosage information, in 1350, a plunger is moved in the tip segment to deliver the proper dosage of the substance. The second input starts the drug delivery process. The controller uses this second input and the dosage information to control the operation of the motor and attached plunger. The control operates the motor to move the plunger a distance that delivers the specified dosage. Optionally, the controller may also use the dosage information to control the rate at which the motor moves the plunger.

In 1360, an indication that the substance has been delivered is provided. This indication can be in the form of an illuminated LED. Optionally, an indication that the substance has reached the proper temperature range can be provided by illuminating an LED as well. Further, the controller may also ensure that the substance has reached the proper temperature before the substance is delivered. In such a case, the controller does not allow the second input to commence the delivery process until the substance has reached the proper temperature range.

Figure 14:
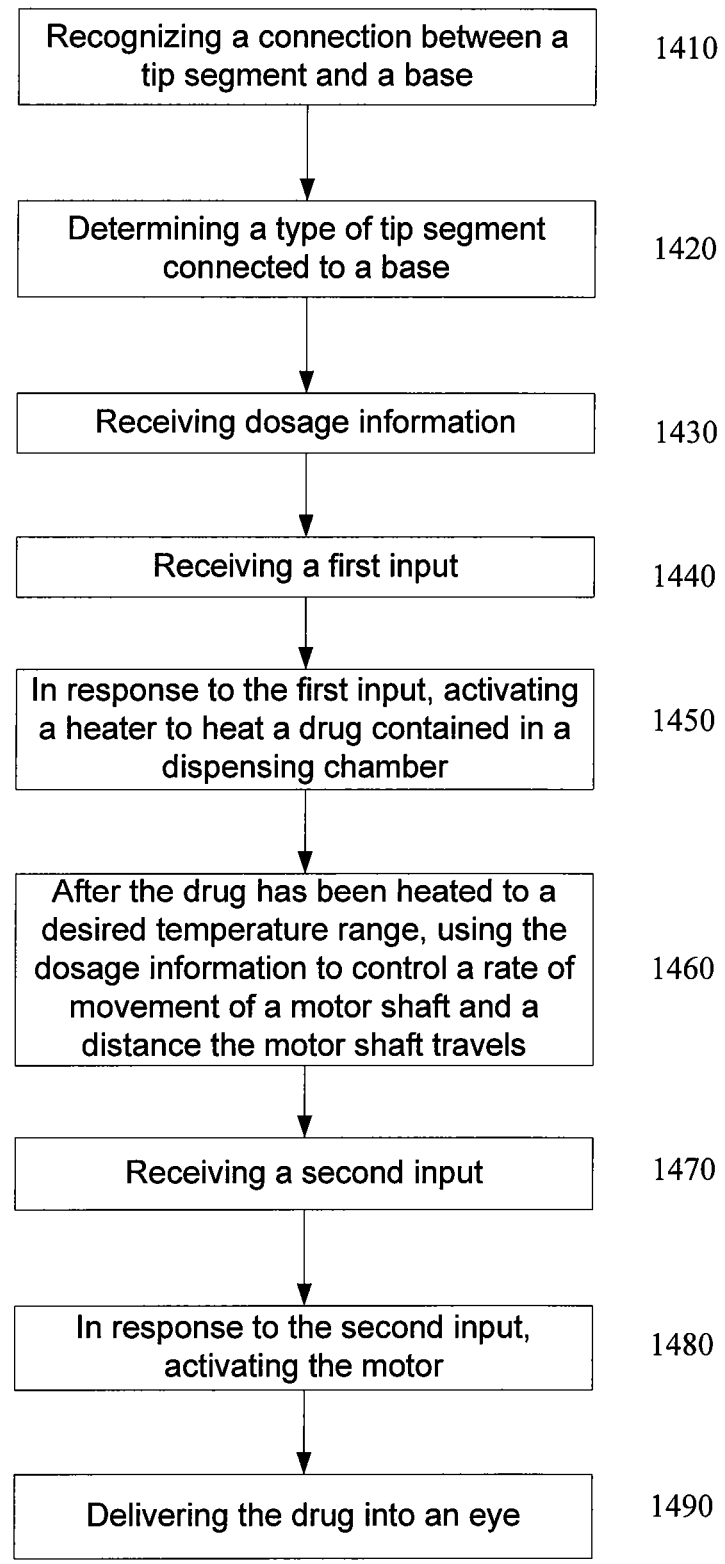
FIG. 14 is a block diagram of a method of operating a drug delivery hand piece according to an embodiment of the present invention.

FIG. 14 is a block diagram of a method of operating a drug delivery hand piece according to an embodiment of the present invention. In 1410, a connection between a tip segment and a limited reuse assembly is recognized. Typically, a medical professional attaches the tip segment to the limited reuse assembly by, for example, screwing the tip segment onto the limited reuse assembly. This connection is recognized by an electrical or RF connection between the tip segment and the limited reuse assembly. For example, when the tip segment contains an RFID tag and the limited reuse assembly contains an RFID reader, the connection is recognized by the limited reuse assembly when the RFID reader in the limited reuse assembly reads information from the RFID tag in the tip segment. In other embodiments, an electrical or data interface connects the tip segment to the limited reuse assembly to allow information to be read from the tip segment by the controller in the limited reuse assembly.

In 1420, the type of tip segment is determined by the limited reuse assembly. Typically, the controller receives information about the type of tip segment. This information is typically stored in or on the tip segment itself. When the tip segment is connected to the limited reuse assembly, the controller receives information about the type of tip segment. The controller can use the information about the type of tip segment to select an algorithm to control the tip segment. In 1430, the limited reuse assembly also receives dosage information. This dosage information is received by the controller in a similar fashion.

In 1440, a first input is received. Typically, this first input is generated via a switch or button located on the hand piece. For example, a surgeon may activate a switch to turn the heater on. In response to this first input, in 1450, a heater is activated to heat a drug contained in a dispensing chamber. Typically, current is provided to the heater and controlled by the controller.

After the drug has been heated to the desired temperature range, in 1460, the dosage information is used to control the rate of movement and distance the plunger travels. In 1470, a second input is received. Typically, this second input is generated via a switch or button located on the hand piece. For example, a surgeon may press a button to begin the delivery of the substance. The second input is only accepted by the hand piece after the drug has reached the proper temperature range. In this manner, the initiation of the drug delivery is only enabled after the drug has reached the proper temperature range. This prevents the administration of the drug when it is not in the proper temperature range. As noted above, delivering the drug only when it is in the proper temperature range may be necessary for efficacy.

In response to this second input and based on the dosage information, in 1480, the motor is activated to move the plunger the tip segment to deliver the proper dosage of the drug. The second input starts the drug delivery process. The controller uses this second input and the dosage information to control the operation of the motor and attached plunger. The control operates the motor to move the plunger a distance that delivers the specified dosage. Optionally, the controller may also use the dosage information to control the rate at which the motor moves the plunger. In 1490, the drug is delivered into the eye from the tip segment.

Optionally, an indication that the substance has been delivered can be provided. This indication can be in the form of an illuminated LED. Further, an indication that the substance has reached the proper temperature range can be provided by illuminating an LED as well.

Figure 15A:
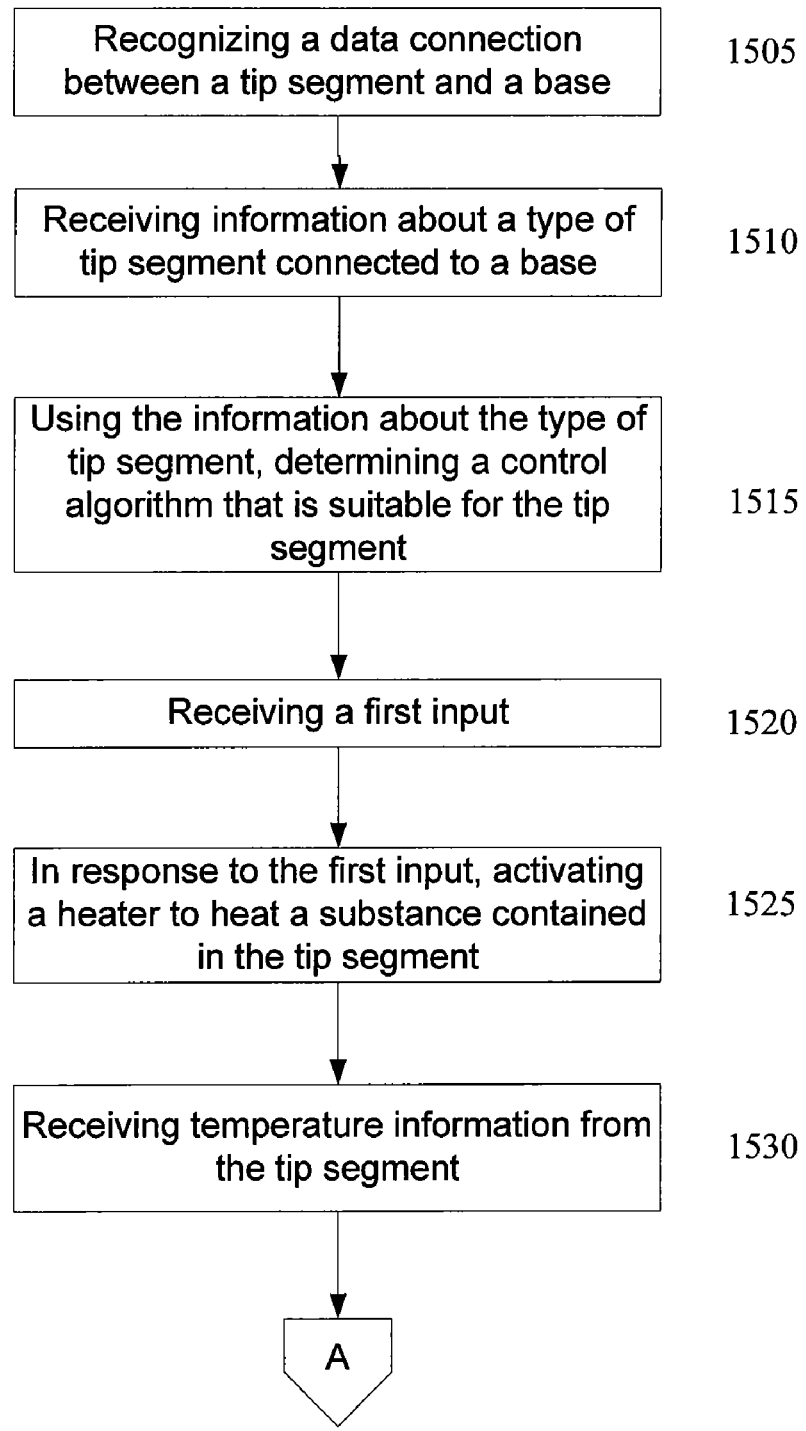
FIGS. 15A & 15B are a block diagram of a method of operating a drug delivery hand piece according to an embodiment of the present invention.
Figure 15B:
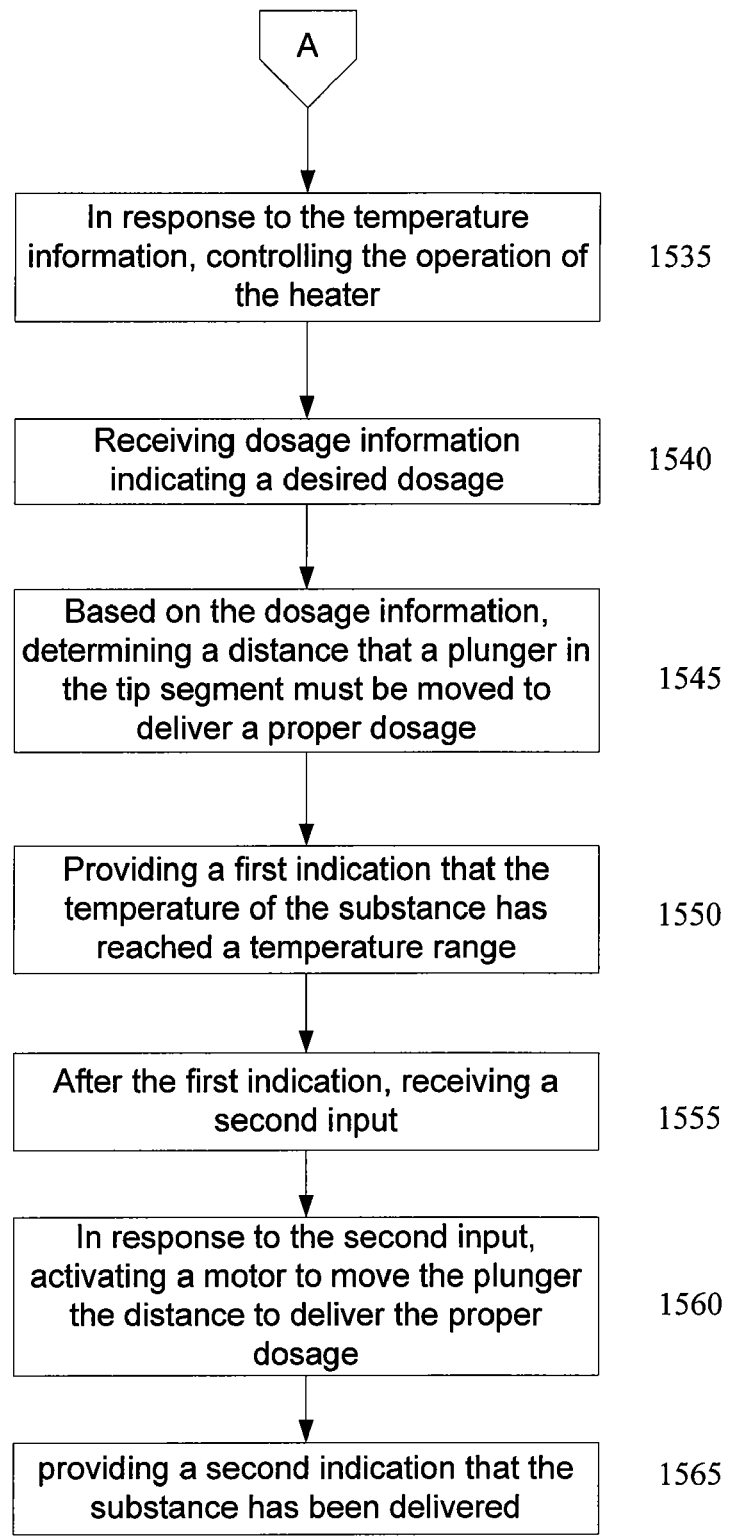

FIGS. 15A & 15B are a block diagram of a method of operating a drug delivery hand piece according to an embodiment of the present invention. In 1505 a data connection is recognized between the tip segment and the limited reuse assembly. This data connection can be a wireless connection like an RFID connection, or it can be a wired connection like a data interface. In 1510, the limited reuse assembly receives information about the type of tip segment connected to it. In 1515, using the information about the type of tip segment, the limited reuse assembly selects a suitable control algorithm. The controller may select one of several control algorithms stored in memory.

In 1520, a first input is received. In response to the first input, in 1525, the heater is activated to heat the substance contained in the tip segment. In 1530, the controller receives temperature information from the tip segment. In 1535, the controller controls the operation of the heater using the temperature information. In such a case, the controller is configured to regulate the heater. The controller may control the amount of current to the heater to control the temperature of the substance.

In 1540, the controller receives dosage information. In 1545, the controller, using the dosage information, determines a distance that the plunger in the tip segment must be moved to deliver the proper dosage. In 1550, a first indication that the temperature of the substance has reached the proper temperature range is provided. In 1555, after this first indication is provided, a second input is received. In response to this second input, in 1560, the motor is activated to move the plunger the distance to deliver the proper dosage. In 1565, a second indication that the substance has been delivered is provided.

From the above, it may be appreciated that the present invention provides an improved system and methods for delivering precise volumes of a substance into an eye. The present invention provides a single use, disposable delivery device tip segment that is capable of delivering a precise dosage without reflux. The tip segment interfaces with a universal hand piece limited reuse assembly capable of operating different types of tip segments. The substance that is to be delivered into the eye, typically a drug, is maintained in a temperature range by the temperature control features of the present invention. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ophthalmic injection system comprising:
a tip segment connectable to and removable from a limited reuse assembly, the tip segment comprising:
a dispensing chamber having an inner surface and an outer surface, the inner surface defining a cavity for receiving a quantity of a substance;
a plunger engaged with the inner surface of the dispensing chamber, the plunger capable of sliding in the cavity of the dispensing chamber, the plunger fluidly sealed to the inner surface of the dispensing chamber, the plunger having a proximate end and a distal end; the proximate end having a first mechanical linkage interface;
a heater in proximity to the dispensing chamber;
a data store;
a first tip interface connector electrically coupled to the heater;
a second tip interface connector coupled to the data store; and
a first housing at least partially enclosing the dispensing chamber and the plunger;
the limited reuse assembly comprising:
a power source;
a controller for controlling the operation of the system;
a first limited reuse assembly interface connector, the first limited reuse assembly interface connector capable of interfacing with the first tip interface connector;
a second limited reuse assembly interface connector, the second limited reuse assembly interface connector capable of interfacing with the second tip interface connector;
a motor having a shaft;
a second mechanical linkage interface located on an end of the shaft; and
a second housing at least partially enclosing the controller and the motor;
wherein the first mechanical linkage interface is mateable with the second mechanical linkage interface such that when the tip segment is connected to the limited reuse assembly, the first mechanical linkage interface mates with the second mechanical linkage interface so that motion of the shaft results in motion of the plunger.

2. The system of claim 1 wherein the tip segment further comprises:
a needle fluidly coupled to the dispensing chamber.

3. The system of claim 1 further comprising:
a data interface between the tip segment and the limited reuse assembly, the data interface for transferring information from the tip segment to the limited reuse assembly, the data interface coupled to the second tip interface connector.

4. The system of claim 3 wherein information about the temperature of the heater is transferred from the tip segment to the limited reuse assembly.

5. The system of claim 4 wherein the information about the temperature of the heater is used by the a controller to control operation of the heater.

6. The system of claim 3 wherein dosage information is transferred from the tip segment to the limited reuse assembly.

7. The system of claim 6 wherein the controller uses the dosage information to control the operation of the motor.

8. The system of claim 7 wherein the controller operates the motor such that the shaft is moved a calculated distance thereby displacing the plunger and causing a fixed amount of the substance to exit the dispensing chamber.

9. The system of claim 1 wherein the data store holds dosage information.

10. The system of claim 1 wherein the data store holds information about the type of the tip segment.

11. The system of claim 1 wherein the data store is a semiconductor memory device.

12. The system of claim 1 wherein the data store is an RFID tag.

13. The system of claim 1 wherein the motor is a stepper motor.

14. The system of claim 1 wherein the first mechanical linkage and the second mechanical linkage comprise a ball and socket linkage.

15. The system of claim 1 wherein the tip segment further comprises:
a plunger stop mechanism for limiting movement of the plunger.

16. The system of claim 1 wherein a first amount of the substance is preloaded in the dispensing chamber and a dosage of the substance comprising less than the first amount is delivered by movement of the plunger in the dispensing chamber.

17. The system of claim 16 wherein the controller determines a distance to cause the motor to move the shaft such that movement of the shaft results in the movement of the plunger.

18. The system of claim 1 wherein the controller operates the motor to cause a movement of the plunger in the dispensing chamber such that the substance is delivered at a fixed rate.

19. The system of claim 1 wherein the controller operates the motor to cause a movement of the plunger in the dispensing chamber such that the substance is delivered at a variable rate.

20. The system of claim 12 wherein the limited reuse assembly further comprises:
an RFID reader located within the second housing, the RFID reader adapted to read information from the RFID tag.

21. The system of claim 1 wherein the limited reuse assembly further comprises:
an indicator for indicating a status of the system.

22. The system of claim 21 wherein the indicator is a light emitting diode.

23. The system of claim 1 wherein the limited reuse assembly further comprises:
an input device located on the second housing.

24. The system of claim 23 wherein the input device is a switch.

25. The system of claim 23 wherein the input device is a button.

26. The system of claim 1 wherein the limited reuse assembly further comprises:
a lock mechanism for securing the tip segment to the limited reuse assembly.

27. The system of claim 1 wherein the limited reuse assembly further comprises a first threaded portion and the tip segment further comprises a second threaded portion such that the first threaded portion and the second threaded portion can be screwed together to secure the tip segment to the limited reuse assembly.

28. The system of claim 1 wherein the substance is a drug for treating a condition of the eye.

29. The system of claim 1 wherein the limited reuse assembly is a universal limited reuse assembly capable of being connected to and operating two or more different tip segments that perform different functions.

30. The system of claim 29 wherein the limited reuse assembly is capable of being connected to and operating a tip segment that performs a cauterizing function.

31. The system of claim 1 wherein the tip segment further comprises:
a seal adapted to prevent contamination of the substance.

32. The system of claim 1 wherein the power source is a battery.

33. A disposable drug delivery device comprising:
a dispensing chamber having an inner surface and an outer surface, the inner surface defining a cavity for receiving a quantity of a substance;
a plunger engaged with the inner surface of the dispensing chamber, the plunger capable of sliding in the cavity of the dispensing chamber, the plunger fluidly sealed to the inner surface of the dispensing chamber, the plunger having a proximate end and a distal end; the proximate end having a mechanical linkage interface;
a heater in proximity to the dispensing chamber;
a data store;
a first tip interface connector coupled to the heater;
a second tip interface connector coupled to the data store;
a housing at least partially enclosing the dispensing chamber and the plunger;
wherein the mechanical linkage is mateable with and separable from a limited reuse assembly adapted to drive the plunger.

34. The system of claim 33 wherein the tip segment further comprises:
a needle fluidly coupled to the dispensing chamber.

35. The system of claim 33 wherein the data store holds dosage information.

36. The system of claim 33 wherein the data store holds information about the type of the tip segment.

37. The system of claim 33 wherein the data store is a semiconductor memory device.

38. The system of claim 33 wherein the tip segment further comprises:
an RFID tag located within the first housing.

39. The system of claim 38 wherein the RFID tag has dosage information.

40. The system of claim 38 wherein the RFID tag has information about the type of the tip segment.

41. The system of claim 33 wherein the tip segment further comprises:
a plunger stop mechanism for limiting movement of the plunger.

42. The system of claim 33 wherein movement of the plunger in the dispensing chamber determines a dosage of the substance.

43. The system of claim 33 wherein a first amount of the substance is preloaded in the dispensing chamber and a dosage of the substance comprising less than the first amount is delivered by movement of the plunger in the dispensing chamber.

44. The system of claim 33 wherein a rate of movement of the plunger in the dispensing chamber determines a rate of delivery of the substance.

45. The system of claim 33 wherein the substance is a drug for treating a condition of the eye.

46. The system of claim 33 wherein the tip segment further comprises:
a seal adapted to prevent contamination of the substance.

* * * * *